US011534612B2

(12) United States Patent
Verbeek et al.

(10) Patent No.: US 11,534,612 B2
(45) Date of Patent: Dec. 27, 2022

(54) ADAPTER ASSEMBLIES FOR IMPLANTABLE MEDICAL ELECTRICAL SYSTEMS

(71) Applicant: Medtronic, Inc., Minneapolis, MN (US)

(72) Inventors: Maurice Verbeek, Geleen (NL); Ralph Leinders, Sittard (NL)

(73) Assignee: Medtronic, Inc., Minneapolis, MN (US)

( * ) Notice: Subject to any disclaimer, the term of this patent is extended or adjusted under 35 U.S.C. 154(b) by 826 days.

(21) Appl. No.: 15/923,148

(22) Filed: Mar. 16, 2018

(65) Prior Publication Data

US 2018/0264271 A1    Sep. 20, 2018

Related U.S. Application Data

(60) Provisional application No. 62/472,191, filed on Mar. 16, 2017.

(51) Int. Cl.
*A61N 1/375*      (2006.01)
*A61B 5/00*       (2006.01)

(52) U.S. Cl.
CPC ........... *A61N 1/3752* (2013.01); *A61N 1/375* (2013.01); *A61B 5/686* (2013.01); *A61B 5/6867* (2013.01);
(Continued)

(58) Field of Classification Search
CPC .. A61N 1/375; A61N 1/37512; A61N 1/3752; A61N 1/3758
See application file for complete search history.

(56) References Cited

U.S. PATENT DOCUMENTS

| 4,545,381 A | 10/1985 | Bournay, Jr. et al. |
| 5,334,045 A * | 8/1994 | Cappa ............... A61N 1/375 439/506 |

(Continued)

FOREIGN PATENT DOCUMENTS

| WO | WO 99/16503 A1 | 4/1999 |
| WO | WO 2011/088285 A2 | 7/2011 |

OTHER PUBLICATIONS

International Preliminary Report on Patentability dated Sep. 26, 2019, for International Application No. PCT/US2018/022795; 8 pages.

(Continued)

*Primary Examiner* — Allen Porter
(74) *Attorney, Agent, or Firm* — Mueting Raasch Group

(57) ABSTRACT

Casings for retaining adapter connector modules and implantable electrical devices, and adapter assemblies for retaining implantable medical devices, include first and second opposing plates spaced apart by a gap configured to retain the devices such that sides of the devices are in confronting engagement with the first and second plates when placed the device is held in the gap. The first and second plates may be biased towards one another to assist in retaining the device in the gap. The device and adapter connector module may be arranged such that their thicknesses do not overlap. For example, the device and adapter connector module may be arranged such that a bottom perimeter edge of the adapter connector module abuts or is spaced apart from a top perimeter edge of the device.

12 Claims, 24 Drawing Sheets

(52) U.S. Cl.
CPC ....... *A61B 2562/225* (2013.01); *A61N 1/3758* (2013.01)

(56) References Cited

U.S. PATENT DOCUMENTS

| | | | |
|---|---|---|---|
| 6,226,552 B1* | 5/2001 | Staunton | A61N 1/36014 607/72 |
| 8,162,684 B1 | 4/2012 | Sochor | |
| 2007/0060955 A1* | 3/2007 | Strother | A61N 1/36007 607/2 |
| 2012/0052710 A1 | 3/2012 | Deehr et al. | |
| 2013/0337674 A1* | 12/2013 | Stump | H01R 24/28 439/300 |
| 2014/0275968 A1 | 9/2014 | Stevenson et al. | |
| 2017/0239483 A1* | 8/2017 | Mathur | A61N 1/37241 |

OTHER PUBLICATIONS

International Search Report and Written Opinion dated Jun. 6, 2018 for International Application No. PCT/US2018/022795; 14 pages.

* cited by examiner

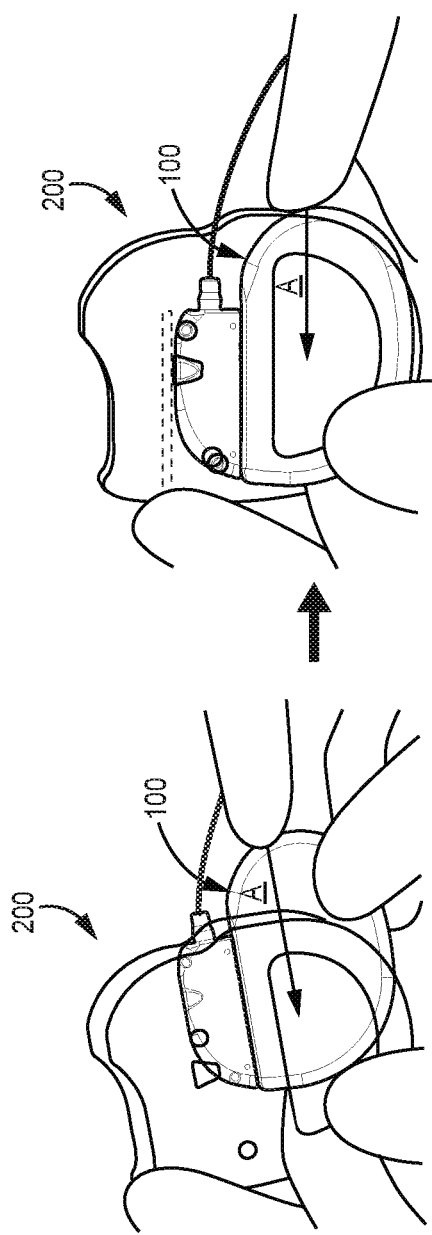
FIG. 2J
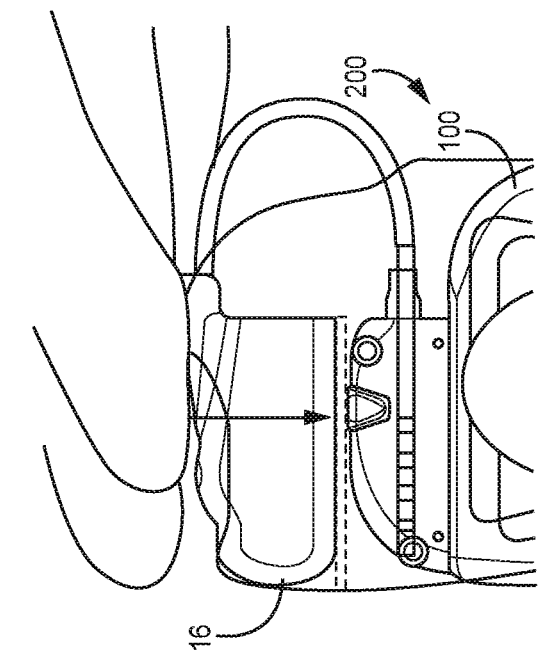
FIG. 2K
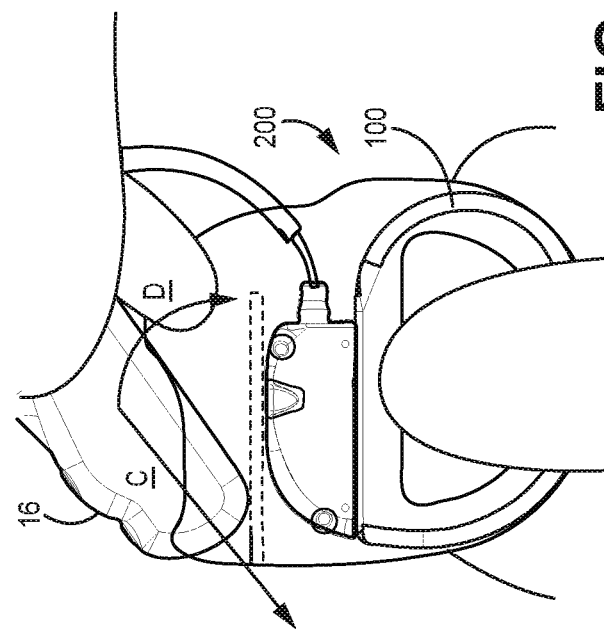

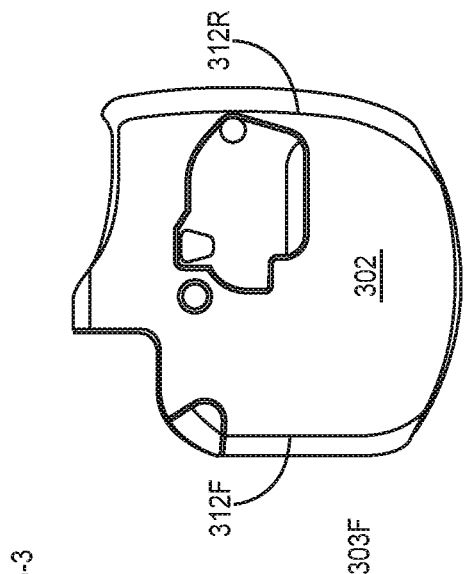
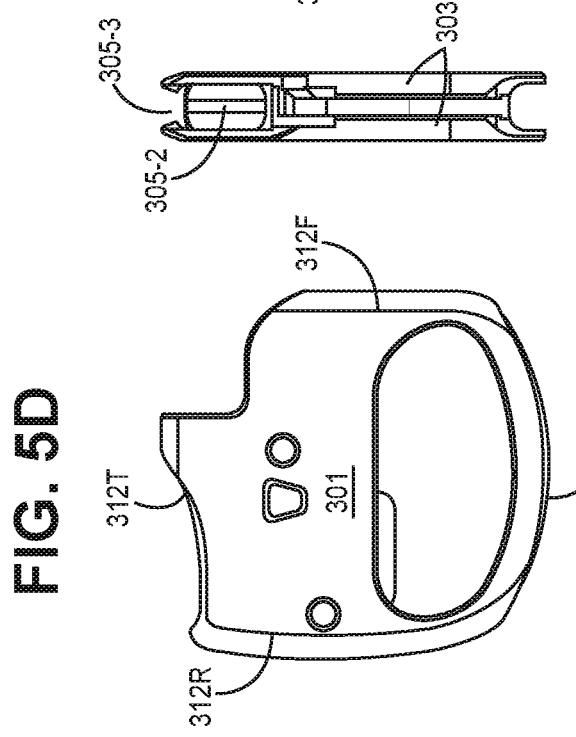
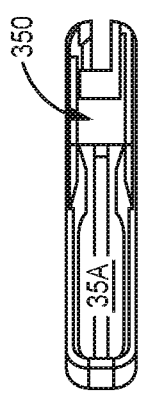
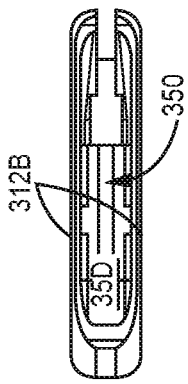
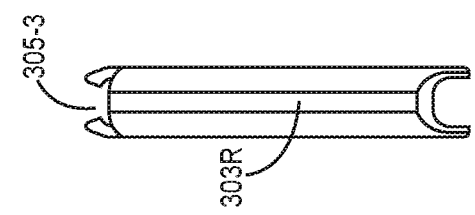

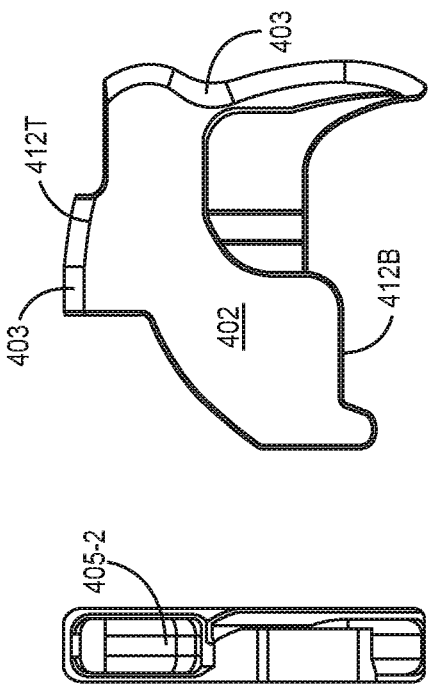
FIG. 7C
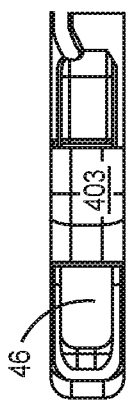
FIG. 7D
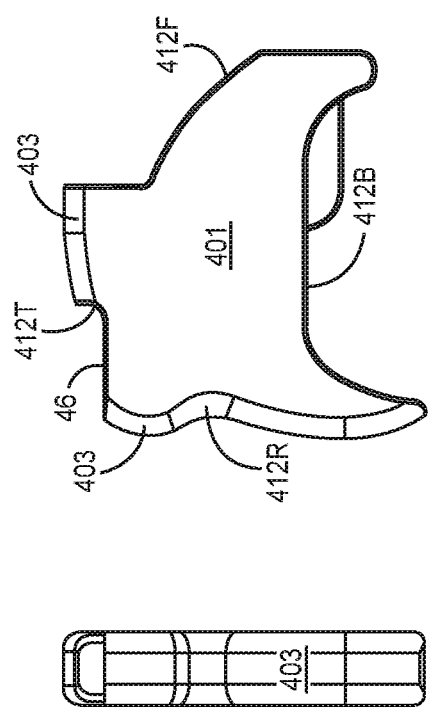
FIG. 7B
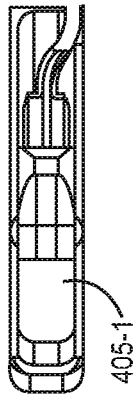
FIG. 7G
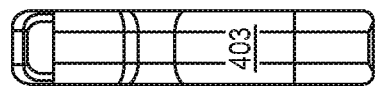
FIG. 7F
FIG. 7E

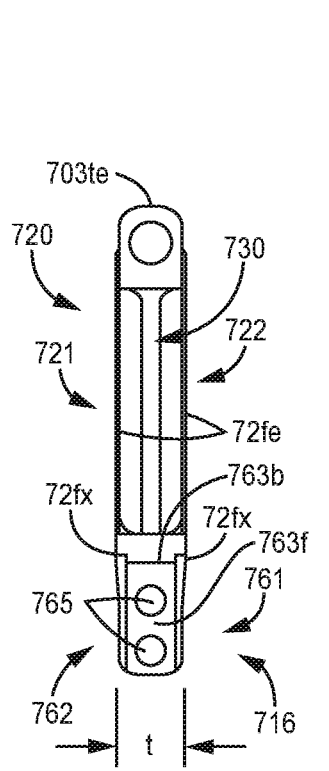
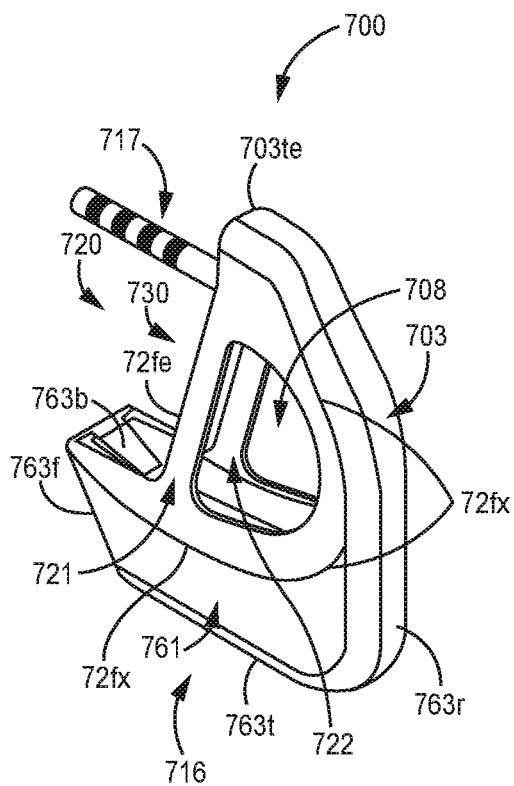
FIG. 13A
FIG. 13B
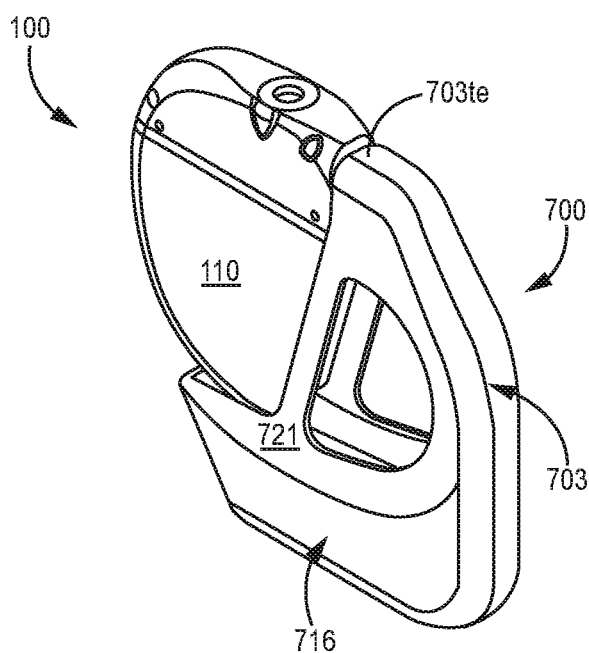
FIG. 13C

ADAPTER ASSEMBLIES FOR IMPLANTABLE MEDICAL ELECTRICAL SYSTEMS

RELATED APPLICATION

This application claims the benefit of U.S. Provisional Patent Application No. 62/472,191, filed on Mar. 16, 2017, the disclosure of which is hereby incorporated herein by reference in its entirety to the extent that it does not conflict with the present disclosure.

TECHNICAL FIELD

The present disclosure is related to implantable medical electrical systems, and more particularly to configurations of adapter assemblies useful for coupling an implantable medical electrical lead to an implantable electrical device and casings for attaching adapters to implantable electrical devices.

BACKGROUND

Implantable medical electrical systems are commonly used to treat conditions such as cardiac arrhythmias, pain, incontinence, sleep disorders, and movement disorders such as Parkinson's disease and epilepsy. Typically, these systems include an elongate implantable medical electrical lead and an implantable pulse generator device, wherein the lead includes one or more electrodes that deliver electrical stimulation from the generator device to target tissue of a patient, when the lead is connected to the device. The generator device is usually implanted in a subcutaneous pocket, for example, formed in the buttock, abdomen or pectoral region of the patient. In some cases, a connection between the lead and the generator device requires an adapter assembly, which is also implanted in the pocket, to make the lead terminal connector compatible with a connector header of the device.

SUMMARY

The present disclosure relates to, among other things, adapter assemblies useful for coupling implantable medical leads to implantable electrical devices with which the leads are not configured to directly couple. Such adapter assemblies may be of use when an implanted electrical device is replaced with a new electrical medical device, and a medical lead that was previously implanted and compatible with the device to be explanted is not directly couplable to the new electrical device to be implanted. The adapter assemblies include an adapter connector module comprising a port configured to couple to the previously implanted lead and include a terminal for connecting the adapter connector module to the new device. The adapter assembly includes a clip comprising first and second plates spaced apart from one another by a gap therebetween. A bottom perimeter edge of the connector module joins the first and second plates to define the gap. The gap is configured to retain the electrical device such that sides of the electrical device are in confronting engagement with the first and second plates.

The present disclosure also relates to casings for retaining an adapter connector module of an adapter and an implantable medical device. The casing includes first and second plates spaced apart from one another by a gap, and a sidewall joining the first and second plates to define the gap. The gap is configured to retain the electrical device and the adapter connector module such that sides of the electrical device are in confronting engagement with the first and second plates.

The electrical device, and adapter assembly or the casing, electrical device, and adapter connector module preferably all fit within the same subcutaneous pocket from which the previous electrical device has been explanted. To provide a suitable long-term experience for the patient, the arrangement of electrical device and adapter assembly or the casing, electrical device, and adapter connector module in the pocket should be as stable and as low profile as possible, for example, to prevent tissue erosion, and the relative positions of electrical device and adapter assembly or the casing, electrical device, and adapter connector module should not result in high stress concentrations that could dislodge any connection between the adapter connector module and the electrical device or between the adapter connector module and the lead. To meet these objectives for the arrangement of device adapter, and lead in the pocket, the instant disclosure sets forth various illustrative embodiments.

In some embodiments, an implantable casing for securing an implantable adapter connector module and an implantable medical device together within a subcutaneous pocket of a patient is described. The casing comprises opposing first and second plates spaced apart from one another by a gap configured to receive the adapter connector module and the medical device. The casing also includes a sidewall joining the first plate to the second plate to define the gap. The gap between the first and second plates has one or more entry openings defined by portions of the first and second plate that are not joined together by the sidewall. The first plate and the second plate are spring biased toward one another such that, when the device and the adapter connector module are received in the gap, sides of the device and adapter connector module are in confronting engagement with, and secured by, the first and second plates and a connector port opening of the adapter connector module faces generally toward one of the one or more entry openings. The gap may be configured to retain the adapter connector module and the device such that a bottom perimeter edge of the adapter connector module abuts or is spaced apart from a top perimeter edge of the device.

In some embodiments, an implantable casing for securing an implantable adapter connector module and an implantable medical device together within a subcutaneous pocket of a patient are described. The adapter connector module has a thickness defined from a first side of the module to a second side of the module. The first and second sides of the module are joined together by a perimeter edge of the module. The module perimeter edge has a rear portion, a front portion, a bottom portion and a top portion. The module includes a connector port having an opening formed in the front portion of the module perimeter edge. The device includes a connector port and has a thickness defined from a first side of the device to a second side of the device. The first and second sides of the device are joined together by a perimeter edge of the device. The device perimeter edge has a rear portion, a front portion, a bottom portion, and a top portion. The device connector port has an opening formed in the front portion of the device perimeter edge. The device connector port opening is located in proximity to the top portion of the device perimeter edge. The casing comprises opposing first and second plates spaced apart from one another by a gap. Each plate has a perimeter edge. The perimeter edge of each plate has a rear portion, a front portion, a bottom portion, and a top portion. The casing also comprises a sidewall joining the first plate to the second plate along one or more perimeter edge portions thereof to define the gap. The gap between the first and second plates has one or more entry openings defined by the first and second plate edge portions that are not joined together by the sidewall. The gap includes a device compartment and an adapter compartment. Each compartment extends from the first plate to the second plate so that, when the device and the adapter connector module are both held in respective compartments, the connector port opening of the adapter connector module faces generally toward one of the one or more entry openings, the first sides of the device and adapter connector module are in confronting engagement with the first plate, the second sides of the device and adapter connector module are in confronting engagement with the second plate, and the thicknesses of the device and adapter connector module do not overlap.

In some embodiments, an adapter assembly for coupling an elongate implantable medical electrical lead to an implantable medical device is described herein. The assembly comprises a connector module including a module connector port comprising one or more internal contacts disposed in a bore for receiving a terminal of the elongate medical lead. The one or more internal contacts each electrically couple to one or more external contacts of a lead terminal when the lead terminal is received in the bore. The assembly further comprises a terminal connector including one or more external contacts and being configured to plug into a connector port of the implantable medical device to electrical couple each external contact to a corresponding internal contact of the device connector port. The assembly also comprises one or more elongate insulated conductors each electrically coupling one of the internal contacts of the connector module connector bore to one of the external contacts of the terminal connector. Additionally, the assembly comprises a clip comprising opposing first and second plates spaced apart from one another by a gap. A bottom perimeter edge of the connector module joins the first plate to the second plate to define the gap. The gap is sized to hold the device therein. The first plate and the second plate are spring biased toward one another such that, when the device is held in the gap, sides of the device are in confronting engagement with, and secured by, the first and second plates. The gap may be configured to retain the device such that the bottom perimeter edge of the connector module abuts or is spaced apart from a top perimeter edge of the device.

In some embodiments, an adapter assembly for coupling an elongate implantable medical electrical lead to an implantable medical device is described herein. The device includes a connector port and having a thickness defined from a first side of the device to a second side of the device. The first and second sides of the device are joined together by a perimeter edge of the device. The device perimeter edge has a rear portion, a front portion, a bottom portion, and a top portion. The device connector port has an opening formed in the front portion of the device perimeter edge. The device connector port opening is located in proximity to the top portion of the device perimeter edge. The assembly comprises a connector module having a thickness defined from a first side of the module to a second side of the module. The first and second sides of the module are joined together by a perimeter edge of the module. The connector module perimeter edge has a rear portion, a front portion, a bottom portion and a top portion. The bottom portion of the module perimeter edge has a curvature conforming to one or more portions of the device perimeter edge. The module includes a connector port. The connector port has an opening formed in the front portion of the module perimeter edge. The adapter assembly further comprises a terminal connector including one or more external contacts and being configured to plug into the device connector port for electrical coupling of each external contact to a corresponding internal contact of the device connector port. The assembly also comprises one or more elongate insulated conductors extending from a first end thereof to a second end thereof. The first end of each conductor is coupled to a corresponding internal contact of the connector module connector bore, and the second end of each conductor is coupled to a corresponding external contact of the terminal connector. Additionally, the assembly comprises a clip comprising opposing first and second plates. The first and second plates are spaced apart from one another by a gap. The gap is sized to hold the device therein so that the first side of the device is in confronting engagement with the first plate and the second side of the device is in confronting engagement with the second plate, and so that the thickness of the device does not overlap the thickness of the connector module. Each of the first and second plates includes a free perimeter edge and a fixed perimeter edge. The first plate extends from the fixed perimeter edge thereof, at the first side of the connector module, and the second plate extends from the fixed perimeter edge thereof, at the second side of the connector module, so that the bottom portion of the module perimeter edge extends between the first and second plates.

BRIEF DESCRIPTION OF THE DRAWINGS

FIG. 2A shows the casing without the electrical device and the adapter connector module. FIG. 2B shows the casing with the electrical device and the adapter connector module held therein.

FIGS. 2J-K are schematic first side views of an embodiment of the casing depicted in FIGS. 2A-B, in which loading of the electrical device (FIG. 2J) and the adapter connector module (FIG. 2K) into the casing are shown.

FIG. 5B is a schematic first side view of an embodiment of the casing depicted in FIG. 5A.

FIG. 5C is a schematic second side view of an embodiment of the casing depicted in FIG. 5A.

FIG. 5D is a schematic top view of an embodiment of the casing depicted in FIG. 5A.

FIG. 5E is a schematic bottom view of an embodiment of the casing depicted in FIG. 5A.

FIG. 5F is a schematic rear view of an embodiment of the casing depicted in FIG. 5A.

FIG. 5G is a schematic front view of an embodiment of the casing depicted in FIG. 5A.

FIG. 7B is a schematic first side view of an embodiment of the casing depicted in FIG. 7A.

FIG. 7C is a schematic second side view of an embodiment of the casing depicted in FIG. 7A.

FIG. 7D is a schematic top view of an embodiment of the casing depicted in FIG. 7A.

FIG. 7E is a schematic bottom view of an embodiment of the casing depicted in FIG. 7A.

FIG. 7F is a schematic rear view of an embodiment of the casing depicted in FIG. 7A.

FIG. 7G is a schematic front view of an embodiment of the casing depicted in FIG. 7A.

FIG. 13A is a schematic front view of an embodiment of an adapter assembly including an adapter connection module and a casing for holding an electrical device.

FIG. 13B is a schematic perspective view of an embodiment of the adapter assembly depicted in FIG. 13A.

FIG. 13C is a schematic perspective view of an embodiment of the adapter assembly depicted in FIG. 13A, in which the device is held in the casing.

DETAILED DESCRIPTION

The following detailed description is illustrative in nature and is not intended to limit the scope, applicability, or configuration of inventive embodiments disclosed herein in any way. Rather, the following description provides practical examples, and those skilled in the art will recognize that some of the examples may have suitable alternatives. Embodiments will hereinafter be described in conjunction with the appended drawings, which are not to scale (unless so stated), wherein like numerals/letters denote like elements. However, it will be understood that the use of a number to refer to a component in a given drawing is not intended to limit the component in another drawing labeled with the same number. In addition, the use of different numbers to refer to components in different drawings is not intended to indicate that the different numbered components cannot be the same or similar to other numbered components. Examples of constructions, materials, dimensions and fabrication processes are provided for select elements and all other elements employ that which is known by those skilled in the art.

Figure 1:
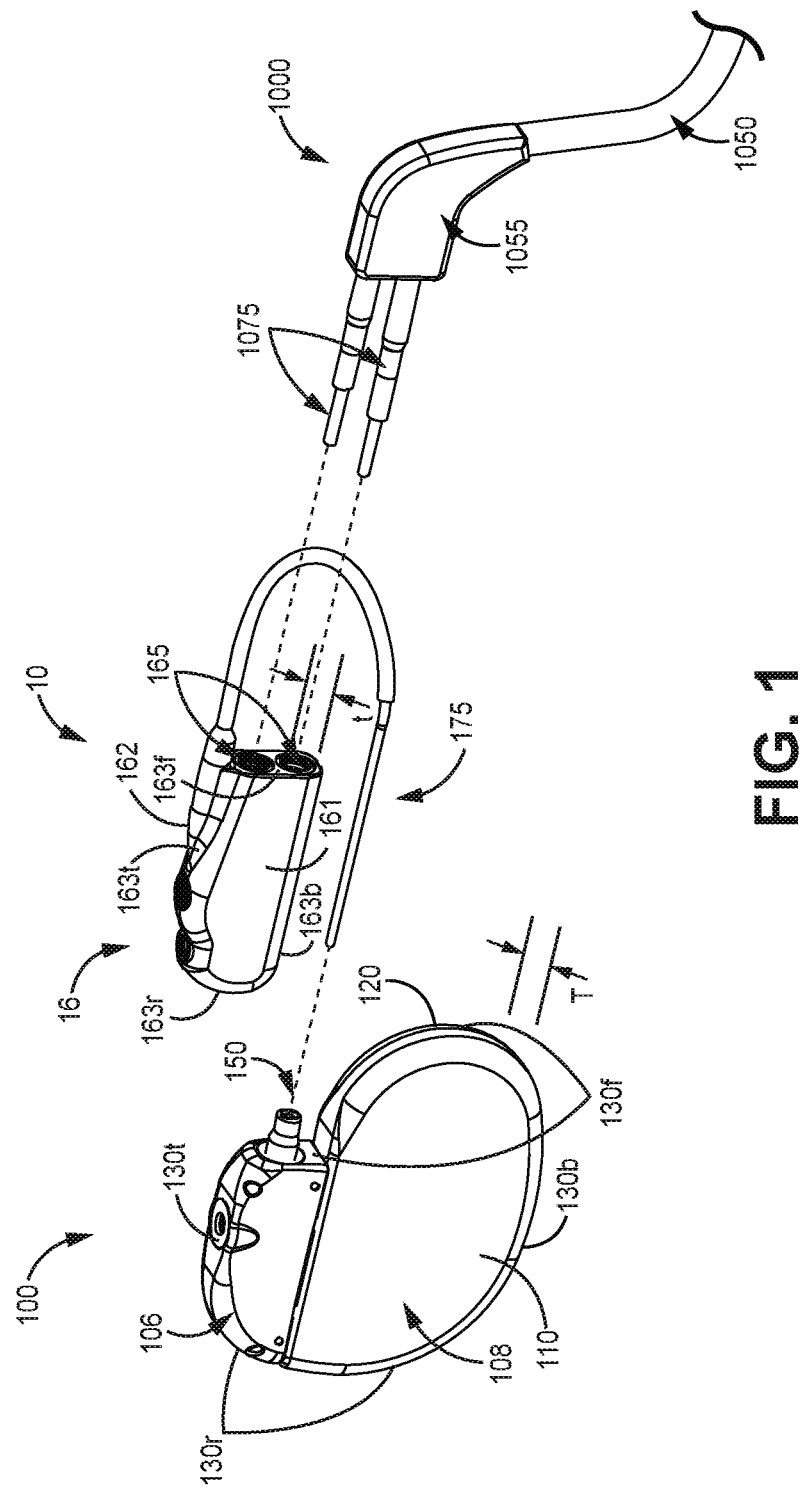
FIG. 1 is a schematic exploded perspective view of an embodiment of an implantable electrical medical system that includes an adapter and an electrical signal generator device.

Reference will now be made in greater detail to various embodiments of the subject matter of the present disclosure, some embodiments of which are illustrated in the accompanying drawings FIG. 1 is an exploded perspective view of an illustrative implantable medical electrical system 100 that includes an elongate lead (or extension) 1000, an adapter 10, and an electrical device 100, all known in the art. The electrical device 100 may be one or both of an electrical signal generating device or an electrical signal receiving device. An example of electrical signal generating device is an electrical pulse generator. An example of an electrical signal receiving device includes a device configured to sense, for example, a physiological parameter of a subject.

Just a proximal portion of lead 1000 is shown in FIG. 1. FIG. 1 illustrates lead 1000 including an elongate body 1050 terminated by grip 1055 from which a pair of terminal connectors 1075 extend. Terminal connectors 1075 of lead 1000 are configured to mate with a device of a different model (not shown) than that of device 100, for example, an older model. With reference to FIG. 1 it can be seen that device 100 includes a single connector port 150 that will not accommodate electrical coupling with terminal connectors 1075. In an implant of the older model device and lead 1000, when a clinician determines that the older model device needs to be replaced by a newer model device, for example, device 100, adapter 10 may be employed to make the implanted lead 1000 compatible with device 100 for electrical coupling therewith. FIG. 1 further illustrates adapter 10 including a connector module 16 that has a pair of connector ports 165, which will accommodate electrical coupling with lead terminal connectors 1075, and a terminal connector 175, which can be plugged into device connector port 150 for electrical coupling therewith. Thus, the already implanted lead 1000 is made compatible with the new device 100.

Device 100, adapter 10, and the illustrated proximal portion of lead 1000 should, preferably, all fit within the same subcutaneous pocket from which the clinician has explanted the old device. To provide a suitable long-term experience for the patient, the arrangement of device 100, adapter 10, and lead 1000 in the pocket is preferably as stable and as low profile as possible, for example, to prevent skin erosion. Furthermore, adapter 10 should be positioned so as not to interfere with telemetry communications between device 100 and an external control unit, and the relative positions of adapter 10, device 100 and lead 1000 should not result in high stress concentrations that could dislodge lead electrodes or impair the electrical coupling between lead 1000 and adapter 10, and/or adapter 10 and device 100. To meet these objectives for the arrangement of device 100, adapter 10, and lead 1000 in the pocket, the instant disclosure sets forth various illustrative embodiments.

First, to facilitate the ensuing descriptions of the various embodiments, device 100 and adapter 10 are more fully defined in conjunction with FIG. 1. Device 100 is shown including a hermetically sealed housing 108 and a connector header 106, in which the aforementioned connector port 150 is formed, wherein header 106 is attached to housing 108. A bulk of header 106 is typically formed from a relatively rigid medical grade polymer, such as polyurethane; and housing 108 is typically formed from a medical grade titanium or stainless steel. Those skilled in the art understand that electrical contacts within connector port 150 are coupled to control circuitry contained within housing 108 via a hermetically sealed feedthrough assembly (not shown). For the purpose of the ensuing descriptions, a first side 110, a second side 120, and a perimeter edge 130 of device 100 encompass housing 108 and header 106 together as a whole. FIG. 1 shows a thickness T of device 100 defined from first side 110 to second side 120 thereof, and perimeter edge 130 of device 100 joining together first and second sides 110, 120, wherein perimeter edge 130 is divided into the following portions: a rear portion 130r, a front portion 130f, a bottom portion 130b, and a top portion 130t. An opening into connector port 150 is shown formed in device perimeter edge front portion 130f, and located in proximity to device perimeter edge top portion 130t, which may be defined by header 106. Device perimeter edge bottom portion 130b is opposite top portion 130t, and device perimeter edge rear portion 130r is opposite front portion 130f.

FIG. 1 further illustrates a perimeter edge 163 of adapter connector module 16 joining a first side 161 thereof to a second side 162 thereof, wherein a thickness t of module 16 is defined from first side 161 to second side 162. Adapter connector module perimeter edge 163 is divided into the following portions: a rear portion 163r, a front portion 163f, which is opposite rear portion 163r, a bottom portion 163b, and a top portion 163t, which is opposite bottom portion 163b. Openings into adapter connector ports 165 are shown formed in module perimeter edge front portion 163f, and access to one or more set screws may be provided along module perimeter edge top portion 163t.

Figure 2A:
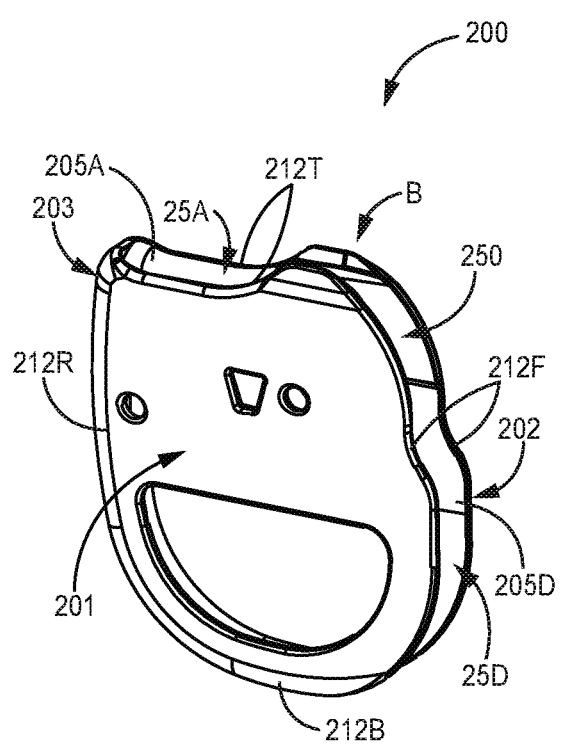
FIGS. 2A-B are schematic perspective views of an embodiment of a casing for holding an implantable electrical device and an adapter connector module together.
Figure 2B:
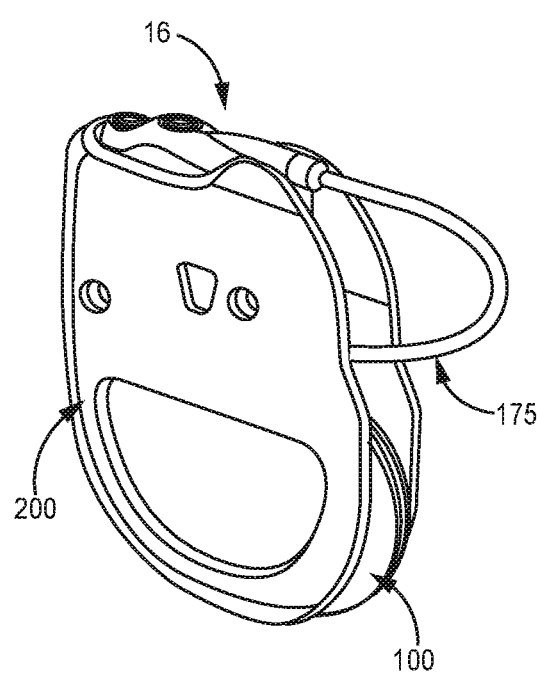
Figure 2D:
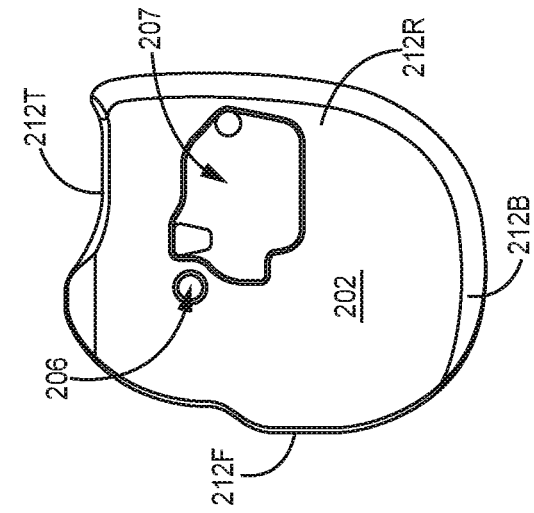
FIG. 2D is a schematic second side elevation view of an embodiment of the casing depicted in FIGS. 2A-B.
Figure 2H:
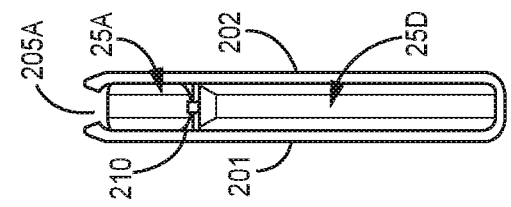
FIG. 2H is a schematic front view of an embodiment of the casing depicted in FIGS. 2A-B.
Figure 2E:
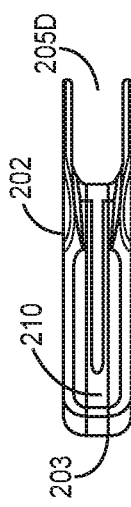
FIG. 2E is a schematic top view of an embodiment of the casing depicted in FIGS. 2A-B.
Figure 2C:
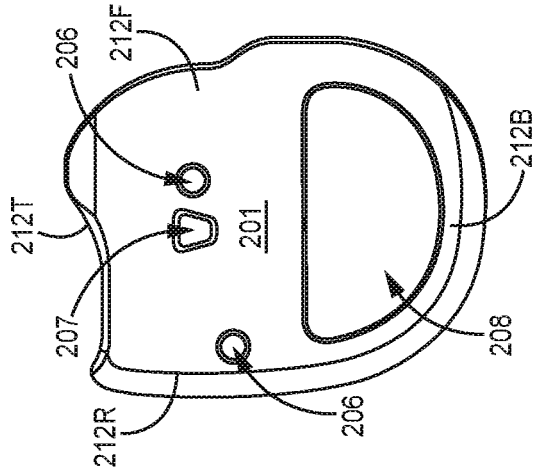
FIG. 2C is a schematic first side elevation view of an embodiment of the casing depicted in FIGS. 2A-B.
Figure 2F:
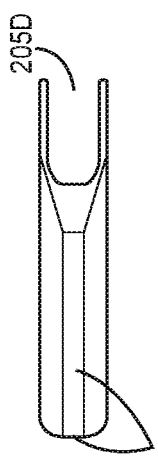
FIG. 2F is a schematic bottom view of an embodiment of the casing depicted in FIGS. 2A-B.
Figure 2G:
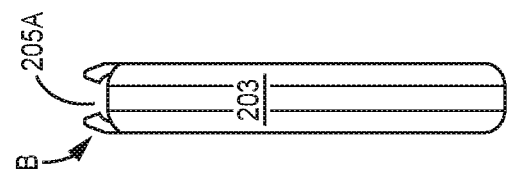
FIG. 2G is a schematic rear view of an embodiment of the casing depicted in FIGS. 2A-B.

FIGS. 2A-B includes two perspective views of a casing 200 for holding device 100 and adapter connector module 16 together in a subcutaneous pocket, according to some embodiments. The first perspective view of FIG. 2A shows casing 200 without device 100 and module 16, and FIG. 2B shows casing 200 with device 100 and module 16 held therein. FIGS. 2C-H is a compilation of first side elevation (FIG. 2C), second side elevation (FIG. 2D), top (FIG. 2E), bottom (FIG. 2F), rear (FIG. 2G) and front (FIG. 2H) views of casing 200. FIGS. 2A-H illustrate casing 200 including a first plate 201 and a second plate 202, each of which includes a perimeter edge 212 divided into the following portions: a rear portion 212R, a front portion 212F, which is opposite rear portion 212R, a top portion 212T, and a bottom portion 212B, which is opposite top portion 212T. FIG. 2AH further illustrate casing 200 including a sidewall 203 that joins first and second plates 201, 202 together, along rear and bottom perimeter edge portions 212R, 212B thereof, such that plates 201, 202 are spaced apart from one another by a gap 250. Entry openings 205D, 205A into gap 250, for example, through which device 100 and adapter connector module 16, respectively, can be inserted into gap 250, are shown being defined by front perimeter edge portions 212F and top perimeter edge portions 212T, respectively, of plates 201, 202.

According to the illustrated embodiment, gap 250 of casing 200 includes a device compartment 25D and an adapter compartment 25A, each of which extend from first plate 201 to second plate 202, so that, when device 100 and adapter connector module 16 are held in respective compartments 25D, 25A, openings of adapter connector module connector ports 165 face generally toward entry opening 205D, each of first and second sides 110, 120 and 161, 162 of device 100 and module 16 are in confronting engagement with the corresponding plate 201, 202, and thicknesses T and t of device 100 and module 16 do not overlap one another.

In some embodiments, a bottom portion of the perimeter edge 163*b* of the connector module 16 may abut or be spaced apart from a top portion of the perimeter edge 130*t* of the device 100.

In some embodiments, a contour of the portion of casing sidewall 203 that extends along device compartment 25D of gap 250 matches that of rear perimeter edge 130*r* of device 100, and may also extend around bottom perimeter edge 130*b* of device 100, when device 100 is held between plates 201, 202. Similarly, the portion of casing sidewall 203 that extends along adapter compartment 25A of gap 250 may match that of rear perimeter edge 163*r* of adapter connector module 16.

According to some embodiments, casing plates 201, 202 are resilient, or elastically deformable, so that plates 201, 202 act as a clip, being spring biased toward one another to secure device 100 and module 16 therebetween. Alternately, or in addition, perimeter edges of plates 201, 202 can bend toward one another, for example, perimeter edge top portions 212T, in the area designated "B" in FIGS. 2A-I, and/or internal surfaces of plates 201, 202 can have inward extending ledges to support edges of device 100 and adapter module 16. With reference to the top and front views of FIGS. 2C-H, internal ledges of plates 201, 202 are shown coming together to form a deck 210 that separates adapter compartment 25A from device compartment 25D in gap 250, according to some embodiments. (Deck 210 is also indicated with dashed lines in FIGS. 2I-K.) Deck 210 is preferably slotted to allow plates 201, 202 to flex away from one another as device 100 and adapter module 16 are positioned therebetween. According to some exemplary embodiments, casing 200 (as well as other casing embodiments described below) is either formed from injection molded medical grade polymer, such as polysulfone or polyurethane, or from a formed medical grade titanium or stainless steel plate.

With further reference to FIGS. 2A-H, according to some embodiments, first plate 201 has an aperture 208 formed therethrough, which is aligned with device compartment 25D of gap 250 to expose a portion of housing 108, when device 100 is held between plates 201, 202. The exposed portion of housing 108 can function as an electrode in the implanted system of device 100, casing 200, lead 1000, and adapter 10. First and second plates 201, 202 may also include one or more apertures 206, each of which is also aligned with device compartment 25D and positioned to allow passage of sutures through corresponding through holes of device header 106, when device 100 is held between plates 201, 202. FIG. 2B further illustrates second plate 202 of casing also including one or more apertures 207 formed therethrough to provide relief, or clearance, for portions of device first and second sides 110, 120 that bulge out of plane from a remainder of sides 110, 120, for example, areas where silicone seals are positioned, such as along first side 110 (seen in FIG. 2K), and that of a junction between header 106 and housing 108 on second side 120 (seen in FIG. 2I).

Figure 2I:
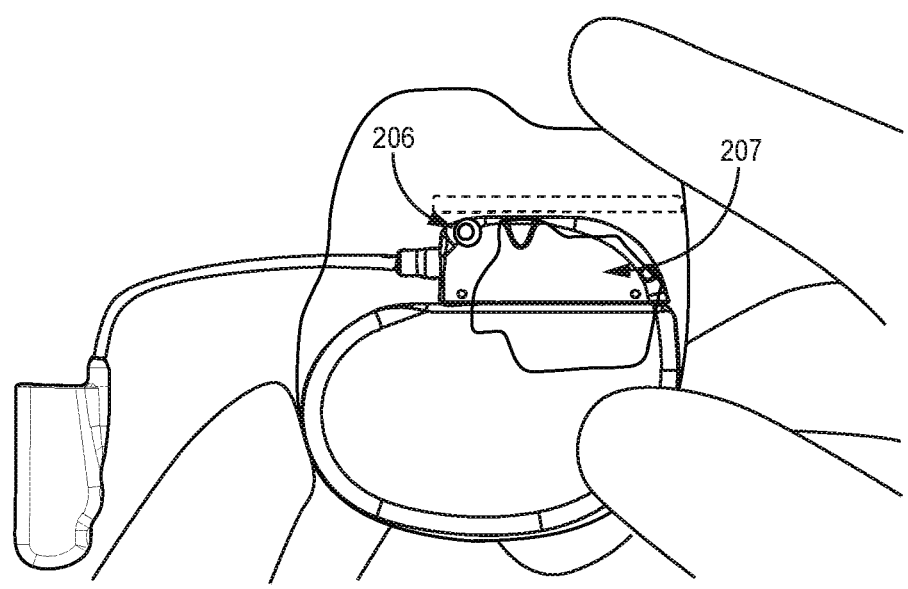
FIG. 2I is a schematic second side view of an embodiment of the casing depicted in FIGS. 2A-B, in which an electrical device is held in the casing.

FIG. 2I-K are schematics showing a loading of device 100 and adapter module 16, respectively, into casing 200. In FIG. 2I device 100 is shown being moved, per arrow A, through entry opening 205D, for loading into device compartment 25D of casing gap 250 (FIGS. 2A-B); and in FIG. 2K adapter module 16 is shown being moved, first through entry opening 205A, per arrow C, and then rotated through entry opening 205A, per arrow D, for loading into adapter compartment 25A of casing gap 250 (FIGS. 2A-B).

Figure 3:
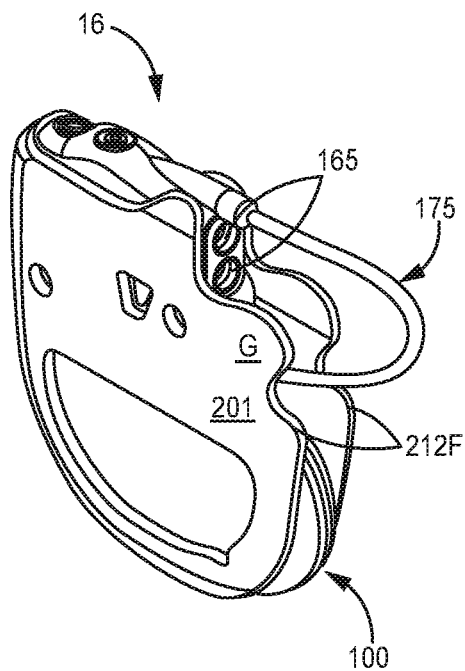
FIG. 3 is a schematic perspective view of an embodiment of a casing holding an electrical device and an adapter connector module.

FIG. 3 is perspective view of an alternate embodiment of casing 200 holding device 100 and adapter connector module 16. FIG. 3 illustrates an alternative contour for front perimeter edge 212F of plates 201, 202 to that shown in FIGS. 2A-H. The alternative contour provides better access to connector ports 165 of adapter module 16, and allows plates 201, 202, at the region designated "G", to support to lead grip 1055 (FIG. 1), when terminal connectors 1075 are plugged into ports 165, while providing clearance for routing of adapter terminal connector 175 around lead grip 1055.

Figure 4A:
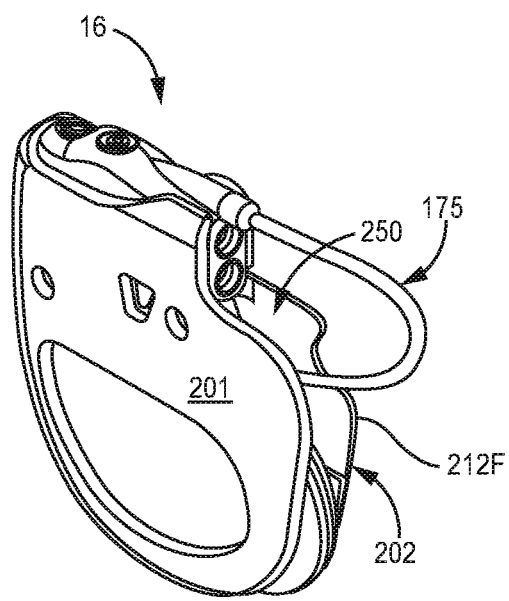
FIG. 4A is a schematic perspective view of an embodiment of a casing holding an electrical device and an adapter connector module.
Figure 4B:
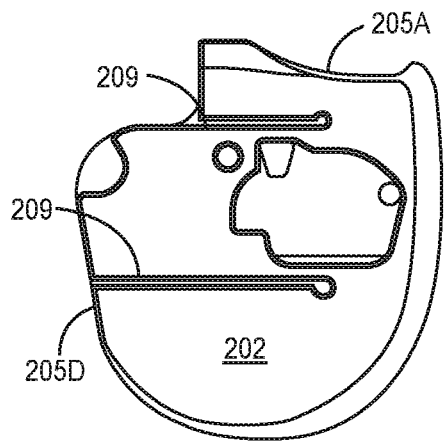
FIG. 4B is a schematic side elevation view of an embodiment of a casing for holding an electrical device and an adapter connector module.

FIG. 4A includes a perspective view of yet another embodiment of casing 200 holding device 100 and adapter connector module 16, and an elevation view the other embodiment of casing 200. FIG. 4A illustrates alternate contours for front perimeter edge 212F of each of first and second plates 201, 202 that differ from one another. The contour of front perimeter edge 212F of second plate 202 provides clearance for routing adapter terminal connector 175, as described above. FIG. 4B further illustrates slots 209 formed through second plate 202, wherein slots 209 enhance a flexibility of plate 202 to increase the ease of inserting device 100 and adapter connector module 16 into gap 250 via entry openings 205D, 205A. Slots 209 may be particularly useful in those embodiments of casing 200 that are formed from medical grade titanium or stainless steel.

Figure 5A:
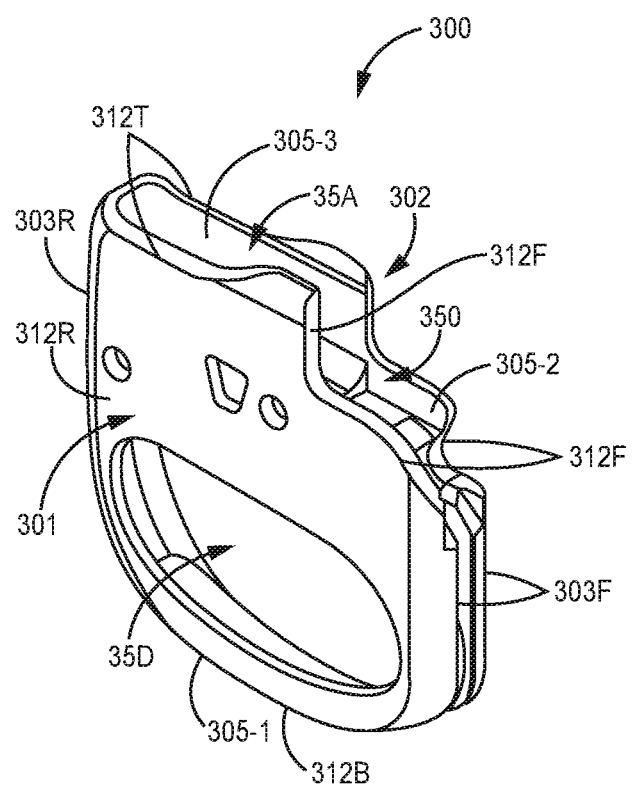
FIG. 5A is a schematic perspective view of an embodiment of a casing for holding an electrical device and an adapter connector module.

FIG. 5A is a perspective view of a casing 300 for holding device 100 and adapter connector module 16 together in a subcutaneous pocket, according to some embodiments. FIGS. 5A-G is a compilation of elevation, top, bottom, rear and front views of casing 300. FIGS. 5A-G illustrate casing 300 including a first plate 301 and a second plate 302, each of which includes a perimeter edge 312 divided into the following portions: a rear portion 312R, a front portion 312F, which is opposite rear portion 312R, a top portion 312T, and a bottom portion 312B, which is opposite top portion 312T. FIGS. 5A-G further illustrate casing 300 including a rear sidewall 303R, which joins first and second plates 301, 302 together, along rear perimeter edge portions 312R, such that plates 301, 302 are spaced apart from one another by a gap 350. Casing 300 is also shown including a front sidewall 303F that is split into opposing parts, each of which extends along a segment of front perimeter edge portion 312F of the corresponding plate 301, 302. Similar to gap 250 of casing 200, gap 350 of casing 300 is divided into a device compartment 35D and an adapter compartment 35A. A first entry opening 305-1 into gap 350, for example, through which device 100 can be inserted into gap 350, is shown being defined by bottom perimeter edge portions 312B of plates 301, 302. A second entry opening 305-2 into gap 350 is shown being defined by front perimeter edge portions 312F, where front sidewall 303F does not extend, and provides access to ports 165 of adapter connector module 16, when held in adapter compartment 35A, so that lead terminal connectors 1075 can be plugged in as shown in the perspective view of FIG. 5H. A third entry opening 305-3 into gap 350, for example, through which adapter connector module 16 can be inserted into gap 350, is shown being defined by top perimeter edge portions 312T.

Figure 5H:
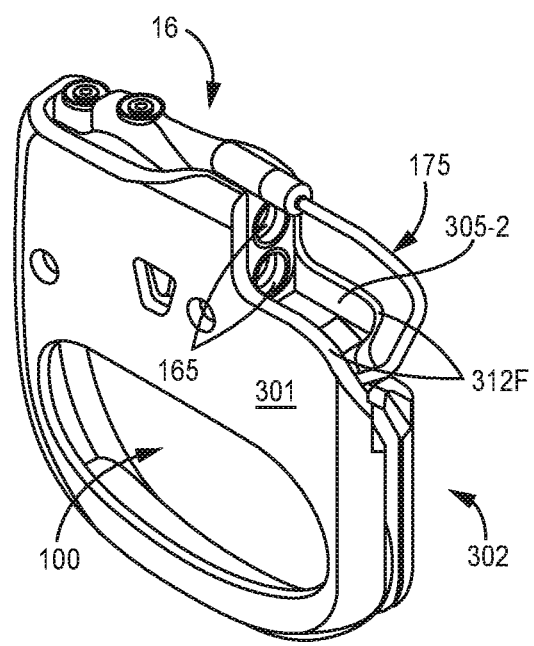
FIG. 5H is a schematic perspective view of an embodiment of the casing depicted in FIG. 5A, in which the electrical device and the adapter connector module are held in the casing.

FIG. 5H illustrates device 100 and adapter module 16 being held by casing 300, in respective compartments 35D, 35A of gap 350, in a similar fashion to that described above for casing 200, so that openings of adapter connector module connector ports 165 face generally toward entry opening 305-2, each of first and second sides 110, 120 and 161, 162 of device 100 and module 16 are in confronting engagement with the corresponding plate 301, 302, and thicknesses T and t of device 100 and module 16 do not overlap one another. In some embodiments, a bottom portion of the perimeter edge 163b of the module 16 may abut or be spaced apart from a top portion of the perimeter edge 130t of the device 100.

FIG. 5H further illustrates front perimeter edge portion 312F of second plate 302 having a contour similar that of the embodiment of casing 200 that is shown in FIG. 2K, for example, to provide clearance for routing of adapter terminal connector 175 around lead grip 1055, to plug terminal 175 into device connector port 150.

Figure 6A:
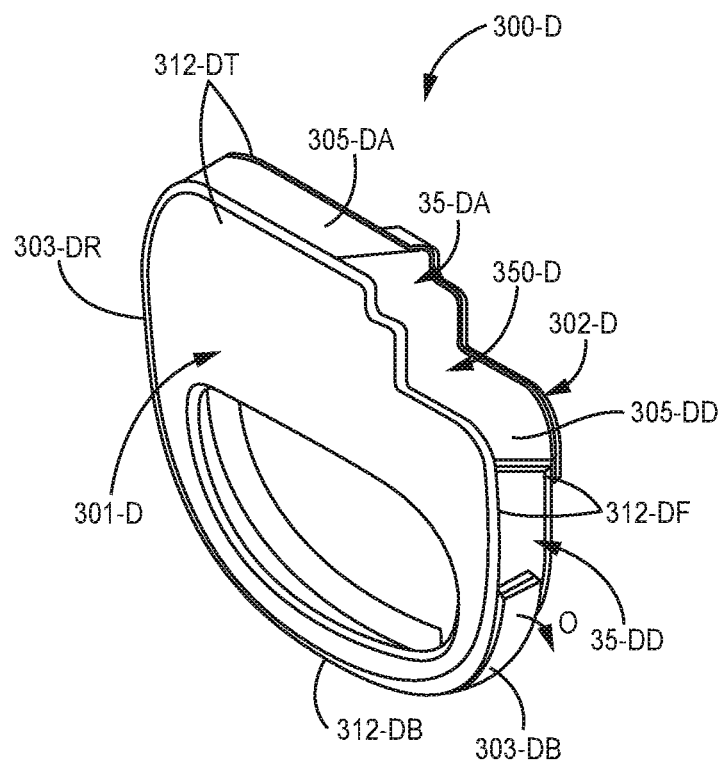
FIG. 6A is a schematic perspective view of an embodiment of a casing for holding an electrical device and an adapter connector module.
Figure 6B:
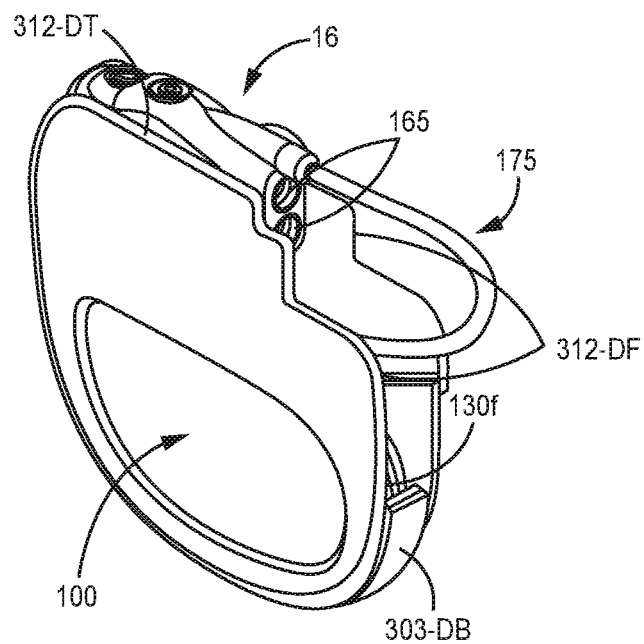
FIG. 6B is a schematic perspective view of an embodiment of the casing depicted in FIG. 6A, in which the electrical device and the adapter connector module are held in the casing.

FIGS. 6A-B includes two perspective views of a casing 300-D for holding device 100 and adapter connector module 16 together in a subcutaneous pocket, according to some embodiments. The first perspective view of FIGS. 6A-B shows casing 300-D without device 100 and module 16, and the second perspective view shows casing 300-D with device 100 and module 16 held therein. FIGS. 6A-B illustrates casing 300-D including a first plate 301-D and a second plate 302-D, each of which includes a perimeter edge 312-D divided into the following portions: a rear portion 312-DR, a front portion 312-DF, which is opposite rear portion 312-DR, a top portion 312-DT, and a bottom portion 312-DB, which is opposite top portion 312-DT. FIGS. 6A-B further illustrates casing 300-D including a rear sidewall 303-DR and a bottom sidewall 303-DB, which join first and second plates 301-D, 302-D together, along rear perimeter edge portions 312-DR and bottom perimeter edge portions 312-DB, such that plates 301-D, 302-D are spaced apart from one another by a gap 350-D. Gap 350-D of casing 300-D is divided into a device compartment 35-DD and an adapter compartment 35-DA. An entry opening 305-DD, through which device 100 can be inserted into compartment 35-DD of gap 350-D, is shown being defined by front perimeter edge portions 312-DF of plates 301-D, 302-D, and an entry opening 305-DA, through which adapter connector module 16 can be inserted into compartment 35-DA of gap 350-D, is shown being defined by top perimeter edge portions 312-DT. According to some embodiments, all or a portion of bottom sidewall 303-DB may be free from first and second plates 301-D, 302-D and elastically deformable to open outward, per arrow O, when inserting device 100 into compartment 35-DD. Then, when device 100 is within compartment 35-DD bottom sidewall 303-DB will spring back to wrap around device perimeter edge front portion 130f.

Figure 7A:
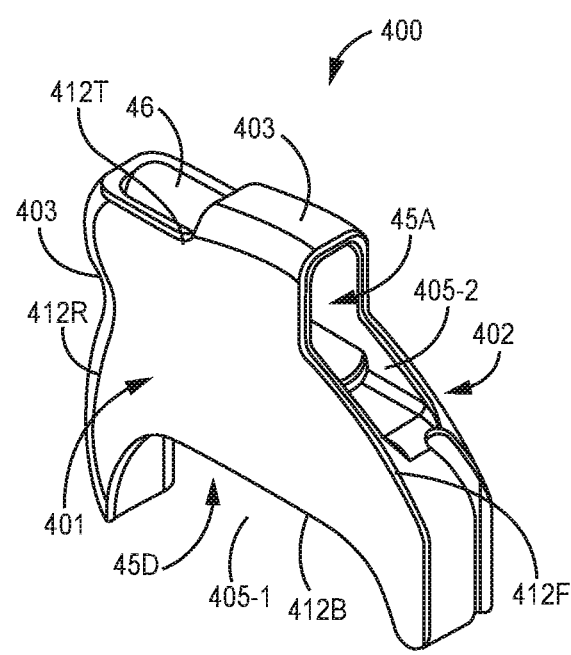
FIG. 7A is a schematic perspective view of an embodiment of a casing for holding an electrical device and an adapter connector module.
Figure 7H:
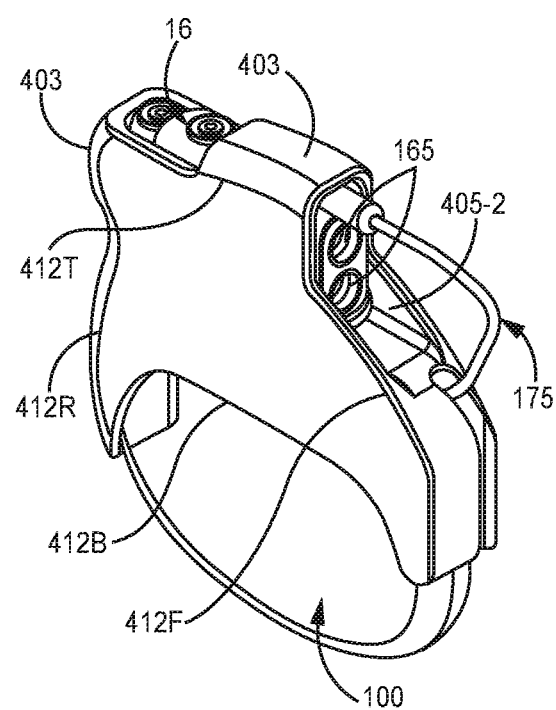
FIG. 7H is a schematic perspective view of an embodiment of the casing depicted in FIG. 7A, in which the electrical device and the adapter connector module are held in the casing.

FIG. 7A is a perspective view of a casing 400, according to some embodiments, for holding device 100 and adapter connector module 16 together in a subcutaneous pocket, according to some embodiments. FIGS. 7B-G is a compilation of elevation, top, bottom, rear and front views of casing 400. FIGS. 7A-G illustrate casing 400 including a first plate 401 and a second plate 402, each of which includes a perimeter edge 412 divided into the following portions: a rear portion 412R, a front portion 412F, which is opposite rear portion 412R, a top portion 412T, and a bottom portion 412B, which is opposite top portion 412T. FIGS. 4A-B further illustrate casing 400 including a sidewall 403 that joins first and second plates 401, 402 together, along rear and top perimeter edge portions 412R, 412T thereof, such that plates 401, 402 are spaced apart from one another by a gap that is divided into a device compartment 45D and an adapter compartment 45A. Sidewall 403 is shown including an aperture 46 formed therethrough, being aligned with adapter compartment 45A, for example, to provide access to set screw ports of adapter connector module 16, when module 16 is held between plates 401, 402 in adapter compartment 45D, as shown in the perspective view of FIG. 7H. A first entry opening 405-1 into device compartment 45D, through which device 100 can be inserted, is shown being defined by bottom perimeter edge portions 412B of plates 401, 402. A second entry opening 405-2 into adapter compartment 45A, through which adapter connector module 16 can be inserted, is shown being defined by front perimeter edge portions 412F. Second entry opening 405-2 also provides access to ports 165 of adapter connector module 16, as shown in FIG. 7H.

According to another category of embodiments, some or all of the above-described embodiments may be modified into adapter assemblies that include casing 200, 300, 400 and adapter 16, wherein casing first and second plates 201, 202, 301, 302, 401, 402, are integrally formed with first and second sides 161, 162 of adapter connector module 16. Additional embodiments in this category are described below, in conjunction with FIGS. 8A-20.

Figure 8A:
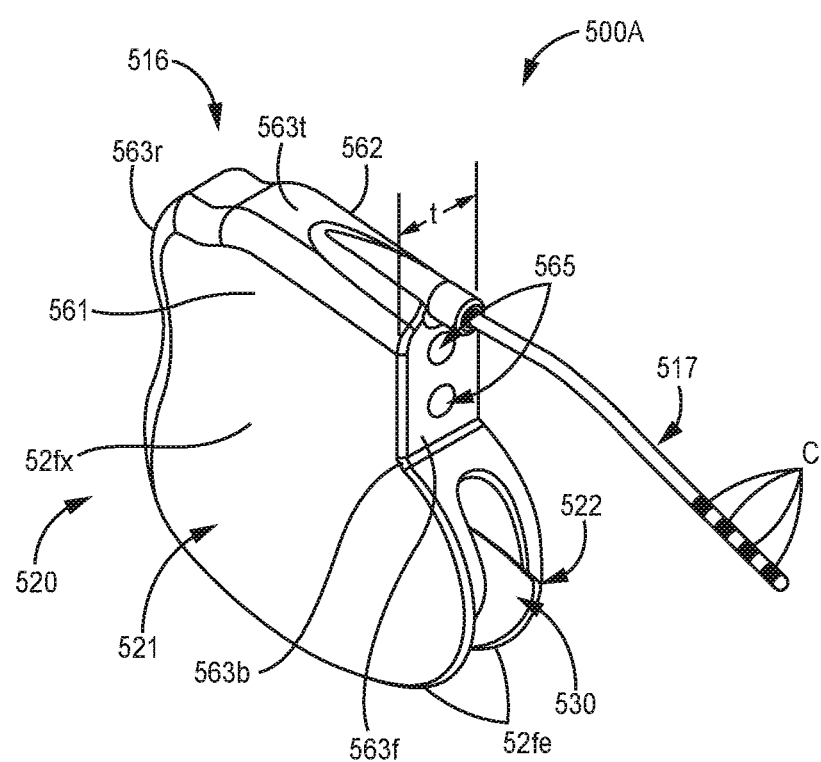
FIG. 8A is a schematic perspective view of an embodiment of an adapter assembly including an adapter connection module and a casing for holding an electrical device.
Figure 8B:
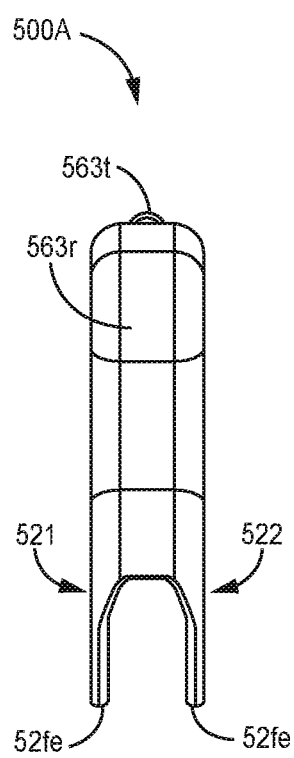
FIG. 8B is a schematic rear view of an embodiment of an adapter assembly depicted in FIG. 8A.
Figure 8C:
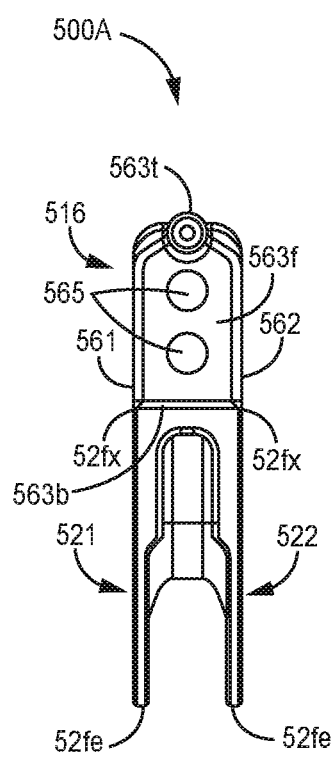
FIG. 8C is a schematic front view of an embodiment of an adapter assembly depicted in FIG. 8A.

FIG. 8A is a perspective view of an adapter assembly 500A, according to some embodiments, for coupling a medical electrical lead, such as lead 1000 (FIG. 1), to an implantable medical device, such as device 100. FIGS. 8B-C includes a rear and a front view of assembly 500A. FIGS. 8A-C illustrate assembly 500A including a connector module 516, a terminal connector 517, and a clip 520 formed by opposing first and second elastically deformable plates 521, 522. Connector module 516 is shown having a thickness t defined from a first side 561 of module 516 to a second side 562 of module 516, and each of opposing first and second plates 521, 522 of clip 520 is shown extending from a fixed perimeter edge 52fx thereof, joined at a corresponding module side 561, 562, to a free perimeter edge 52fe thereof. First and second sides 561, 562 of module 516 are joined together by a perimeter edge 563 that has rear portion 563r, a front portion 563f, which is opposite rear portion 563r, a top portion 563t, and a bottom portion 563b, which is opposite top portion 563t, and which extends between first and second plates 521, 522 of clip 520. Connector ports 565 of module 516, for example, accommodating electrical coupling with lead terminal connectors 1075 (FIG. 1), are shown having openings formed in perimeter edge front portion 563f; and terminal connector 517 of module 516 is shown extending from perimeter edge front portion 563f in proximity to perimeter edge top portion 563t.

Figure 8D:
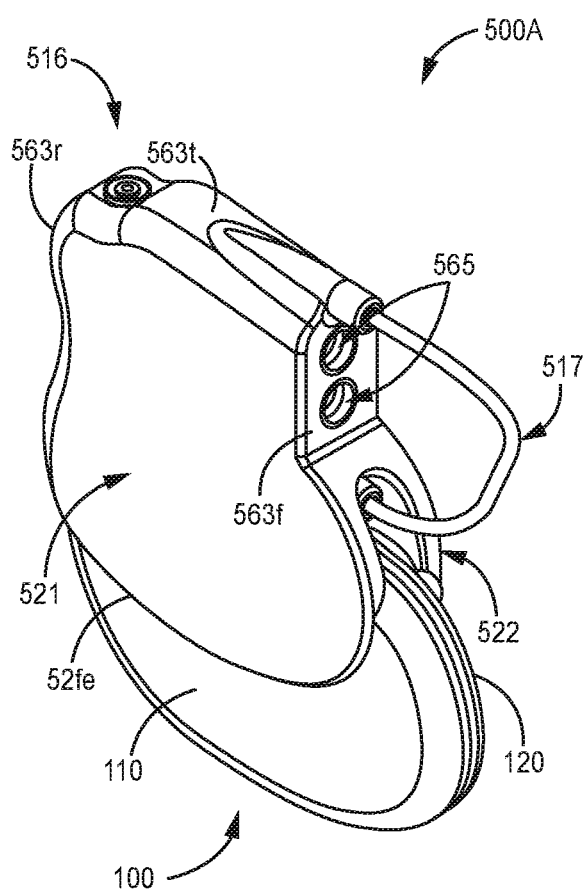
FIG. 8D is a schematic perspective view of an embodiment of an adapter assembly depicted in FIG. 8A, in which the electrical device is held in the casing.

According to the illustrated embodiment, a gap 530 between clip plates 521, 522 is sized to hold device 100 therein so that device first side 110 is in confronting engagement with first plate 521 and device second side 120 is in confronting engagement with second plate 522, for example, as illustrated in FIG. 8D. With reference to FIG. 8D, it should be understood that device perimeter edge top portion 130t is positioned in proximity to module perimeter edge bottom portion 563b so that the opening of device connector port 150 faces in the same direction as the openings of module connector ports 565. Module perimeter edge bottom portion 563b, in some embodiments, has a curvature conforming to device perimeter edge top portion 130t. Each of the aforementioned external contacts C make electrical contact with the aforementioned electrical contacts within device connector port 150, when terminal connector 517 is plugged into port 150, as shown in FIG. 8D. It should be understood that one or more elongate insulated conductors (not shown) extend within an elongate flexible body that joins module 516 to terminal connector 517, and each of the conductors has a first end coupled to a corresponding internal electrical contact of ports 565 and a second end coupled to a corresponding external contact C of terminal connector 517. According to some alternate embodiments, in lieu of the flexible body, a relatively rigid housing or sidewall, which may be integrally formed with the connector module, holds the elongate insulated conductors, for example, as described below in conjunction with FIGS. 9A-C, 10A-C, 11, 12, 13A-C, 14, 15, 16A-C, 17A-C, 18, 19, and 20.

Figure 9A:
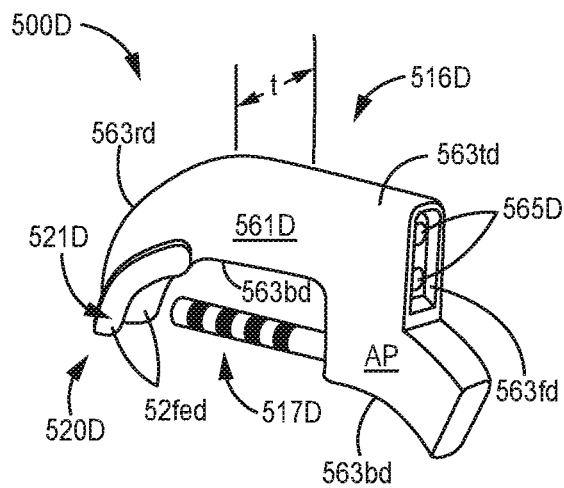
FIGS. 9A-B are schematic perspective views of an embodiment of an adapter assembly including an adapter connection module and a casing for holding an electrical device.
Figure 9B:
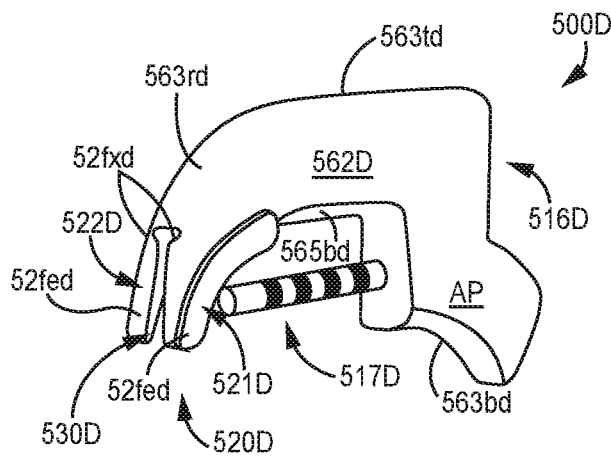

FIGS. 9A-B includes two perspective views of an adapter assembly 500D, according to some embodiments. FIGS. 9A-B illustrates assembly 500D including a connector module 516D, a terminal connector 517D, and a clip 520D formed by opposing first and second plates 521D, 522D. Connector module 516D is shown having a thickness t defined from a first side 561D to a second side 562D thereof, and each of opposing first and second plates 521D, 522D of clip 520D is shown extending from a fixed perimeter edge 52fxd thereof, at a corresponding module side 561D, 562D, to a free perimeter edge 52fed thereof. First and second sides 561D, 562D of module 516D are joined together by a perimeter edge 563D that has rear portion 563rd, a front portion 563fd, which is opposite rear portion 563rd, a top portion 563td, and a bottom portion 563rd, which is opposite top portion 563td, and which extends between first and second plates 521D, 522D of clip 520D. Connector ports 565D of module 516D, for example, accommodating electrical coupling with lead terminal connectors 1075 (FIG. 1), are shown having openings formed in perimeter edge front portion 563fd. It should be understood that elongate insulated conductors extend with module 516D and terminal connector 517D to electrically couple each internal electrical contact of ports 565D to a corresponding external contact of terminal connector 517D.

Figure 9C:
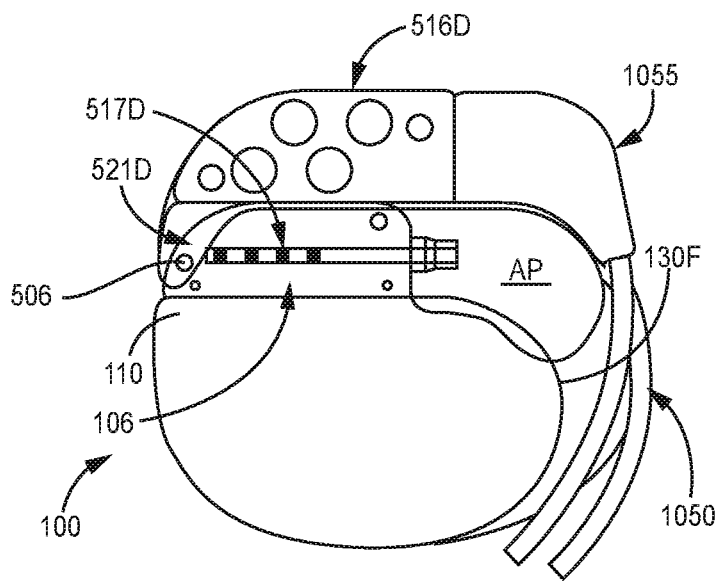
FIG. 9C is a schematic side view of an embodiment of an adapter assembly depicted in FIGS. 9A-B, in which the device is held in the casing.

According to the illustrated embodiment, a gap 530D between clip plates 521D, 522D is sized to hold device 100 therein so that device first side 110 is in confronting engagement with first plate 521D and device second side 120 is in confronting engagement with second plate 522D when terminal connector 517D is plugged into device connector port 150, for example, as illustrated in FIG. 5E. With reference to FIGS. 1 and 9A-C, device perimeter edge top portion 130t is positioned in proximity to module perimeter edge bottom portion 563bd so that the opening of device connector port 150 faces in the same direction as the openings of module connector ports 565D. Plates 521D, 522D, as illustrated in FIG. 9C, may include apertures 506 that align with a suture hole of device header 106. FIGS. 9A-C further illustrate module 516D including an auxiliary portion AP extending below connector ports 565D such that module perimeter edge bottom portion 563bd extends along device perimeter edge front portion 130f, preferably having a curvature that conforms thereto.

Figure 10A:
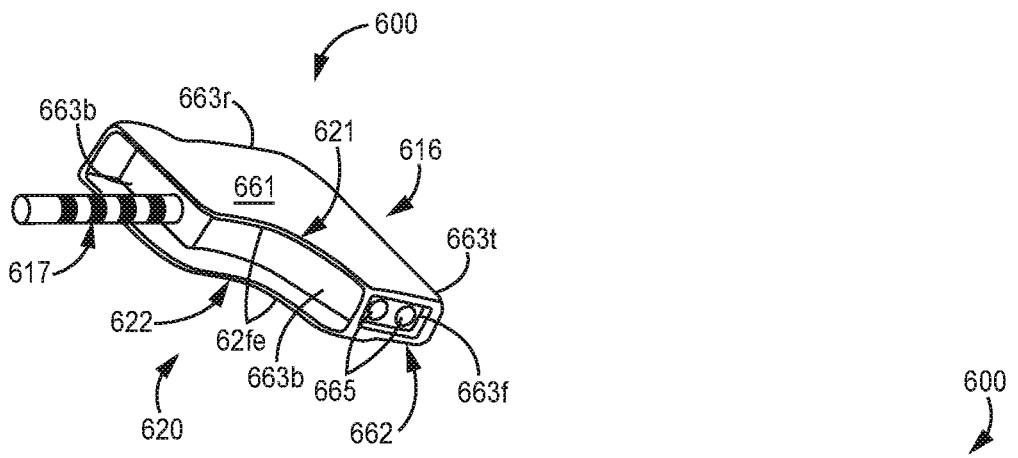
FIGS. 10A-B are schematic perspective views of an embodiment of an adapter assembly including an adapter connection module and a casing for holding an electrical device.
Figure 10B:
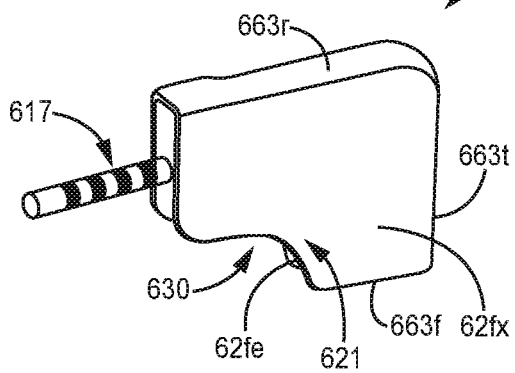

FIGS. 10A-B includes two perspective views of an adapter assembly 600. FIGS. 10A-B illustrates assembly 600 including a connector module 616, a terminal connector 617, and a clip 620 formed by opposing first and second plates 621, 622. Each plate 621, 622 of clip 620 is shown extending from a fixed perimeter edge 62fx thereof, at a corresponding module side 661, 662, to a free perimeter edge 62fe thereof. First and second sides 661, 662 of module 616 are joined together by a perimeter edge 663 that has rear portion 663r, a front portion 663f, which is opposite rear portion 663r, a top portion 663t, and a bottom portion 663r, which is opposite top portion 663t, and which extends between first and second plates 621, 622 of clip 620. Connector ports 665 of module 616, for example, accommodating electrical coupling with lead terminal connectors 1075 (FIG. 1), are shown having openings formed in perimeter edge front portion 663f. It should be understood that elongate insulated conductors extend with module 616 and terminal connector 617 to electrically couple each internal electrical contact of ports 665 to a corresponding external contact of terminal connector 617.

Figure 10C:
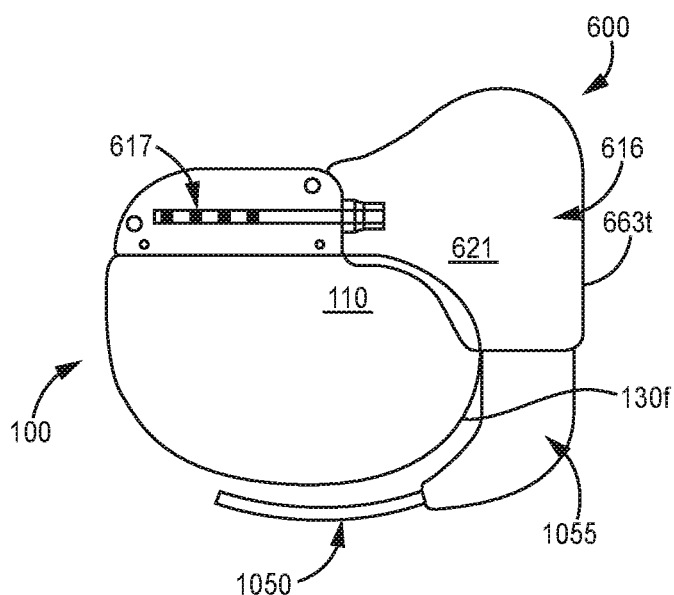
FIG. 10C is a schematic side view of an embodiment of an adapter assembly depicted in FIGS. 10A-B, in which the device is held in the casing.

According to the illustrated embodiment, a gap 630 between clip plates 621, 622 is sized to hold device 100 therein so that device first side 110 is in confronting engagement with first plate 621, and device second side 120 is in confronting engagement with second plate 622, when terminal connector 617 is plugged into device connector port 150, for example, as illustrated in FIG. 10C. With reference to FIG. 10C, device perimeter edge front portion 130f is positioned in proximity to module perimeter edge bottom portion 663b so that the opening of device connector port 150 faces in a direction approximately orthogonal to that in which the openings of module connector ports 665 face. Module perimeter edge bottom portion 663b, in some embodiments, has a curvature conforming to device perimeter edge front portion 130f.

Figure 11:
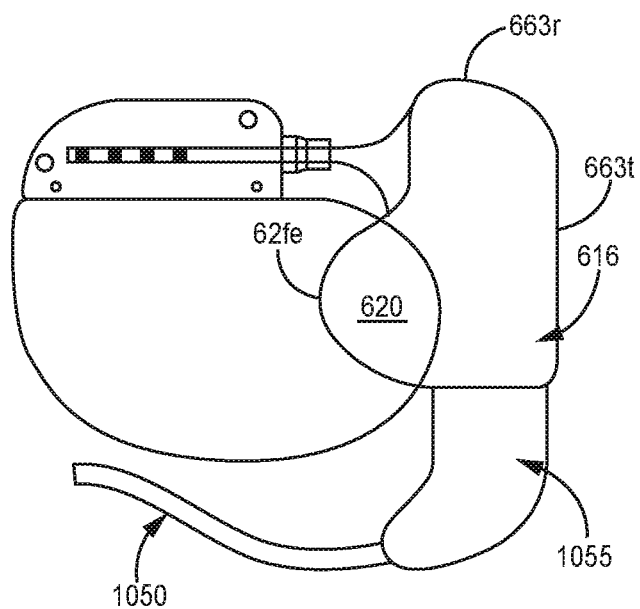
FIG. 11 is a schematic side view of an embodiment of an adapter assembly including an adapter connection module and a casing holding an electrical device.
Figure 12:
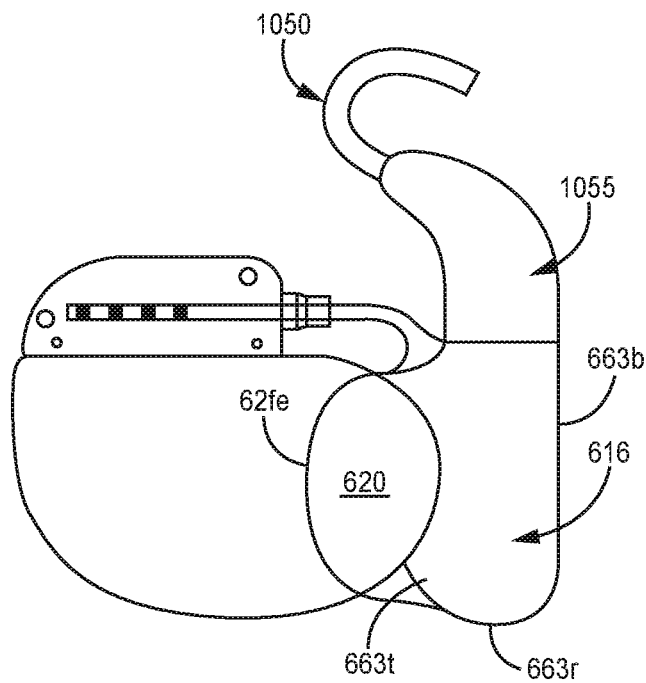
FIG. 12 is a schematic side view of an embodiment of an adapter assembly including an adapter connection module and a casing holding an electrical device.

FIG. 11 shows an alternate embodiment of adapter assembly 600, in which plate free perimeter edges 62fe of clip 620 have an alternative contour. FIG. 12 shows another alternate embodiment of adapter assembly 600, in which plate free perimeter edges 62fe of clip 620 have a similar contour to that shown in FIG. 11, but an orientation of module 616 is reversed so that perimeter edge top portion 663t extends between first and second plates 621, 622.

FIGS. 13A-B includes a front view and a perspective view of an adapter assembly 700, according to some embodiments, for coupling a medical electrical lead, such as lead 1000 (FIG. 1), to an implantable medical device, such as device 100. The views of FIG. 13A-B illustrate assembly 700 including a connector module 716, a terminal connector 717, and a clip 720 formed by opposing first and second plates 721, 722. Connector module 716 is shown having a thickness t defined from a first side 761 of module 716 to a second side 762 of module 716. First and second sides 761, 762 of module 716 are joined together by a perimeter edge 763 that has rear portion 763r, a front portion 763f, which is opposite rear portion 763r, a top portion 763t, and a bottom portion 763b, which is opposite top portion 763t, and which extends between first and second plates 721, 722 of clip 720. Connector ports 765 of module 716, for example, accommodating electrical coupling with lead terminal connectors 1075 (FIG. 1), are shown having openings formed in perimeter edge front portion 763f. Each of opposing first and second plates 721, 722 of clip 720 is shown having a fixed perimeter edge 72fx and a free perimeter edge 72fe. Fixed perimeter edge 72fx of each plate 721, 722 extends along a corresponding module side 761, 762 and along a sidewall 703 of assembly 700, which extends from module perimeter edge rear portion 763r and has a terminal end 703te from which terminal connector 717 extends. It should be understood that one or more elongate insulated conductors (not shown) extend within sidewall 703, and that each of the conductors has a first end coupled to a corresponding internal electrical contact of ports 765 and a second end coupled to a corresponding external contact of terminal connector 717. Module 716, sidewall 703, and plates 721, 722 of adapter assembly 700 may be integrally formed from a relatively rigid medical grade plastic, for example, polysulfone or polyurethane. With further reference to FIGS. 13A-C, according to some embodiments, each plate 701, 702 includes an aperture 708 formed therethrough, for example, to limit the amount of material that forms each plate 701, 702.

According to the illustrated embodiment, a gap 730 between clip plates 721, 722 is sized to hold device 100 therein so that device first side 110 is in confronting engagement with first plate 721 and device second side 120 is in confronting engagement with second plate 722, for example, as illustrated in FIG. 13C. With reference to FIG. 7B, it should be understood that device perimeter edge bottom portion 130b is positioned in proximity to module perimeter edge bottom portion 763b, and device perimeter edge front portion 130f is positioned in proximity to an inner surface of sidewall 703, so that the opening of device connector port 150 faces in an opposite direction to that of the openings of module connector ports 765 to receive terminal connector 717 therein. Module perimeter edge bottom portion 763b and sidewall 703, in some embodiments, each have a curvature conforming to device perimeter edge bottom portion 130b and front portion 130f, respectively. Each of the external contacts of terminal connector 717 make electrical contact with the aforementioned electrical contacts within device connector port 150, when terminal connector 717 is plugged into port 150, as shown in FIG. 13C.

Figure 14:
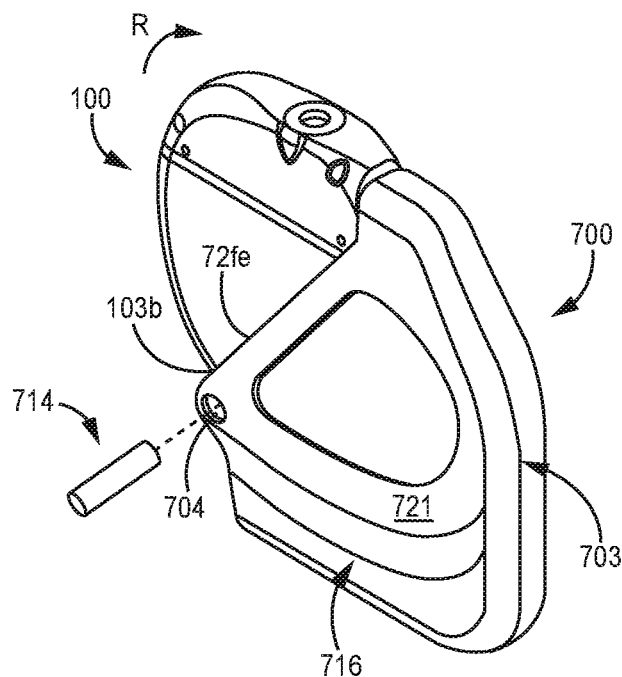
FIG. 14 is a schematic front view of an embodiment of an adapter assembly including an adapter connection module and a casing holding an electrical device.
Figure 15:
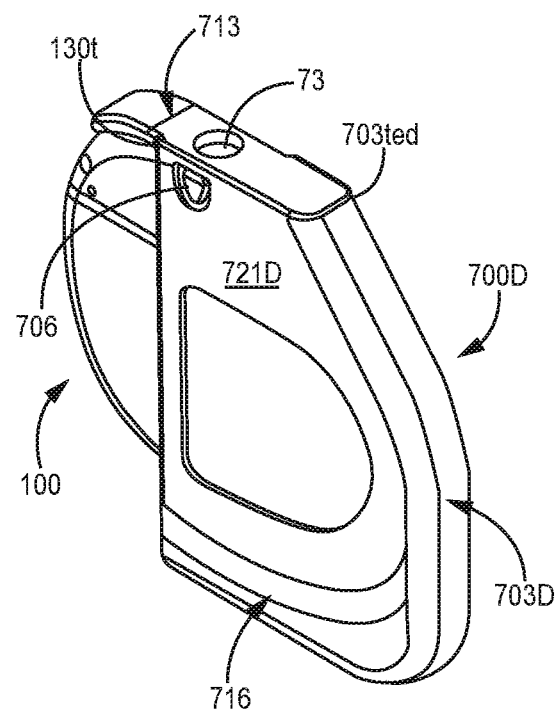
FIG. 15 is a schematic front view of an embodiment of an adapter assembly including an adapter connection module and a casing holding an electrical device.

FIG. 14 is a perspective view of an alternate embodiment of assembly 700 holding device 100, wherein assembly 700 further includes a pin member 714 configured to join together free perimeter edges 72fe of first and second plates 721, 722, for example, via insertion (along dashed line) through aligned apertures 704 thereof, and thereby prevent inadvertent rotation, per arrow R, of device 100 relative to assembly 700. FIG. 15 is a perspective view of an adapter assembly 700D holding device 100, in many respects similar to assembly 700, but including another means to prevent the aforementioned rotation of device 100. Assembly 700D, like assembly 700, includes a clip formed by first and second plates 721D, 722D that extend from adapter 716 in a similar fashion to that of plates 721, 722 of assembly 700. (It should be understood that second plate 722D opposes first plate 721D in the same manner described above for second plate 722 of assembly 700.) Assembly 700D also includes a sidewall 730D through which the aforementioned insulated conductors extend, but a terminal end 730ted of sidewall 703D, from which, it should be understood, terminal connector 717 extends, also has an arm 713 extending therefrom. FIG. 15 illustrates arm 713 extending along perimeter edge top portion 130t of the held device 100 to prevent the aforementioned rotation of device 100. FIG. 15 further illustrates arm 713 including an aperture 73, to provide access to a set screw port of device 100, and plate 721D also including an aperture 706, which may provide relief for a slight bulging of an area where a set screw grommet is positioned. (Plate 722D may also include aperture 706.)

Figures 16A, 16B:
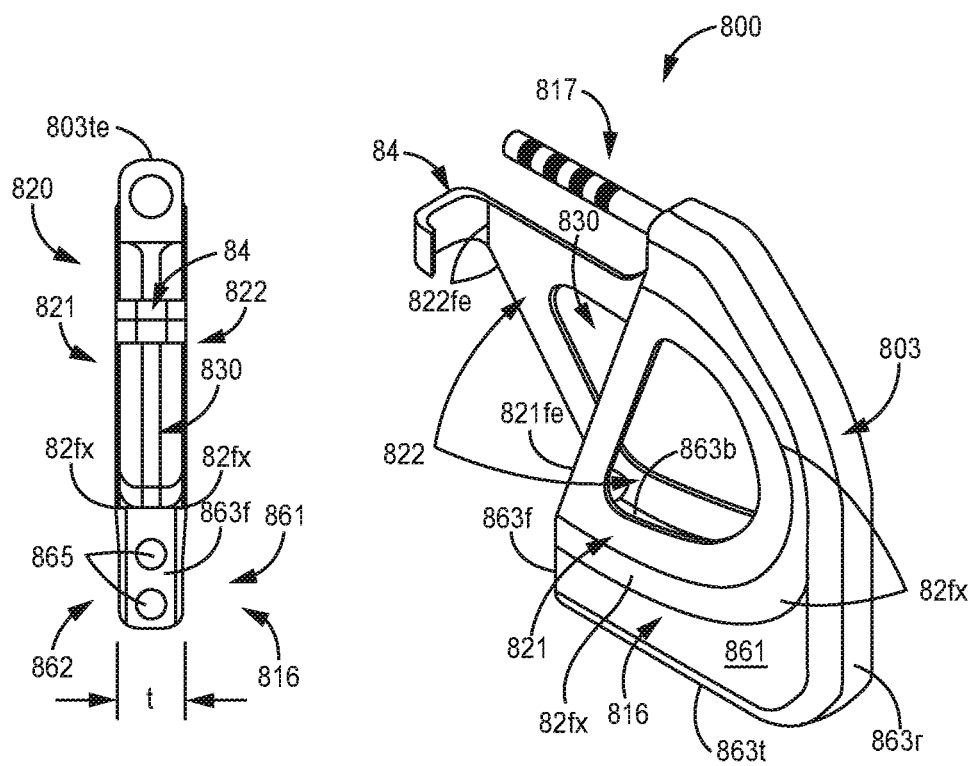
FIG. 16A is a schematic front view of an embodiment of an adapter assembly including an adapter connection module and a casing for holding an electrical device.
FIG. 16B is a schematic perspective view of an embodiment of the adapter assembly depicted in FIG. 16 A.

FIG. 16A-B includes a front view and a perspective view of an adapter assembly 800, according to some embodiments, for coupling a medical electrical lead, such as lead 1000 (FIG. 1), to an implantable medical device, such as device 100. The views of FIGS. 16A-B illustrate assembly 800 including a connector module 816, a terminal connector 817, and a clip 820 formed by opposing first and second plates 821, 822. Connector module 816 is shown having a thickness t defined from a first side 861 of module 816 to a second side 862 of module 816. First and second sides 861, 862 of module 816 are joined together by a perimeter edge 863 that has rear portion 863r, a front portion 863f, which is opposite rear portion 863r, a top portion 863t, and a bottom portion 863b, which is opposite top portion 863t, and which extends between first and second plates 821, 822 of clip 820. Connector ports 865 of module 816, for example, accommodating electrical coupling with lead terminal connectors 1075 (FIG. 1), are shown having openings formed in perimeter edge front portion 863f. Each of opposing first and second plates 821, 822 of clip 820 is shown having a fixed perimeter edge 82fx that extends along a corresponding module side 861, 862 and along a sidewall 803 of assembly 800. Sidewall 803 is shown extending from module perimeter edge rear portion 863r to a terminal end 803te thereof, from which terminal connector 817 extends. It should be understood that one or more elongate insulated conductors (not shown) extend within sidewall 803, and that each of the conductors has a first end coupled to a corresponding internal electrical contact of ports 865 and a second end coupled to a corresponding external contact of terminal connector 817.

Figure 16C:
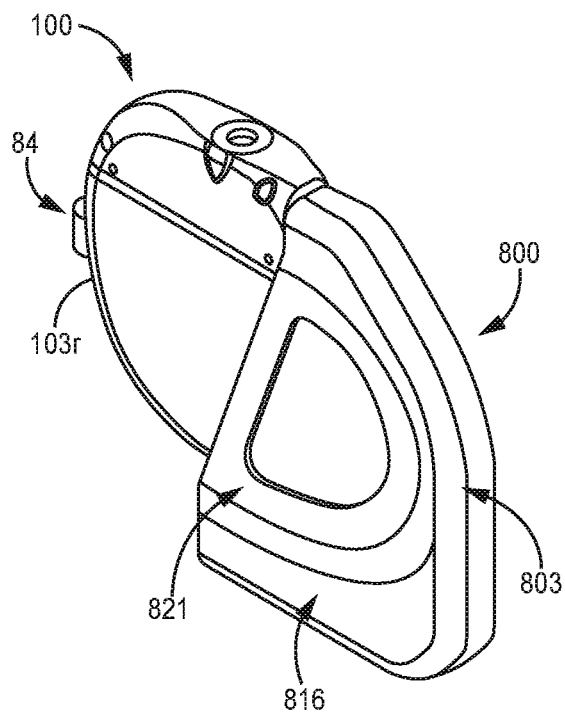
FIG. 16C is a schematic perspective view of an embodiment of the adapter assembly depicted in FIG. 16A, in which the device is held in the casing.

With further reference to FIG. 16A-B, first plate 821 of assembly 800, and a free perimeter edge 821fe thereof, are similar to that of assembly 700, but second plate 822 of assembly 800, and a free perimeter edge 822fe thereof, are more expansive than that of assembly 700. According to the illustrated embodiment, a gap 830 between clip plates 821, 822 is sized to hold device 100 therein so that device first side 110 is in confronting engagement with first plate 821 and device second side 120 is in confronting engagement with second plate 822, for example, as illustrated in FIG. 16C. With reference to FIG. 16C, it should be understood that device perimeter edge bottom portion 130b is positioned in proximity to module perimeter edge bottom portion 863b, and device perimeter edge front portion 130f is positioned in proximity to sidewall 803, so that the opening of device connector port 150 faces in an opposite direction to that of the openings of module connector ports 865 to receive terminal connector 817 therein. Module perimeter edge bottom portion 863b and sidewall 803, in some embodiments, each have a curvature conforming to device perimeter edge bottom portion 130b and front portion 130f, respectively. Each of the external contacts of terminal connector 817 make electrical contact with the aforementioned electrical contacts within device connector port 150, when terminal connector 717 is plugged into port 150, as shown in FIG. 16C. FIGS. 16A-C further illustrate an arm 84 extending from a portion of free perimeter edge 822fe of second plate 822. FIG. 16C shows arm 84 wrapped around perimeter edge rear portion 130r of device 100, when device 100 is held in gap 830 between first and second plates 821, 822, to prevent the above-described inadvertent rotation of device 100 relative to assembly 800.

Figure 17A:
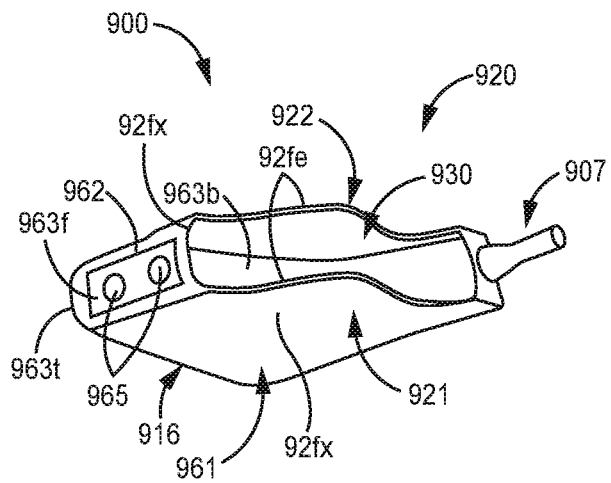
FIG. 17A is a schematic perspective view of an embodiment of an adapter assembly including an adapter connection module and a casing for holding an electrical device.
Figure 17B:
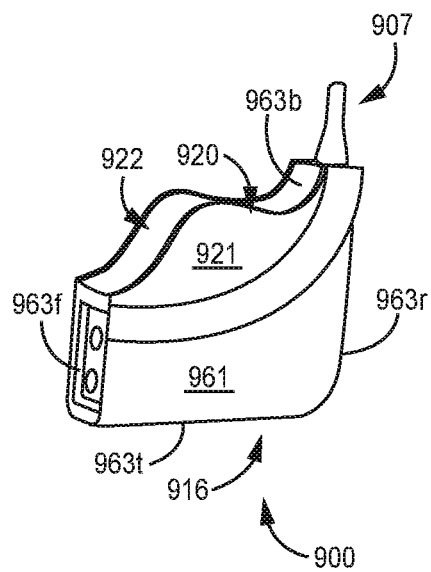
FIG. 17B is a schematic perspective view of an embodiment of the adapter assembly depicted in FIG. 17A.

FIGS. 17A-B includes two perspective views of an adapter assembly 900, according to yet further embodiments, for coupling a medical electrical lead, such as lead 1000 (FIG. 1), to an implantable medical device, such as device 100. The views of FIGS. 17A-B illustrate assembly 900 including a connector module 916 and a clip 920 formed by opposing first and second plates 921, 922. Connector module 916 has a thickness defined from a first side 961 of module 916 to a second side 962 of module 916. First and second sides 961, 962 of module 916 are joined together by a perimeter edge 963 that has rear portion 963r, a front portion 963f, which is opposite rear portion 963r, a top portion 963t, and a bottom portion 963b, which is opposite top portion 963t, and which extends between first and second plates 921, 922 of clip 920. Connector ports 965 of module 916, for example, accommodating electrical coupling with lead terminal connectors 1075 (FIG. 1), are shown having openings formed in perimeter edge front portion 963f. Each of opposing first and second plates 921, 922 of clip 920 is shown having a fixed perimeter edge 92fx and a free perimeter edge 92fe. Fixed perimeter edge 92fx of each plate 921, 922 extends along a corresponding module side 961, 962.

Figure 17C:
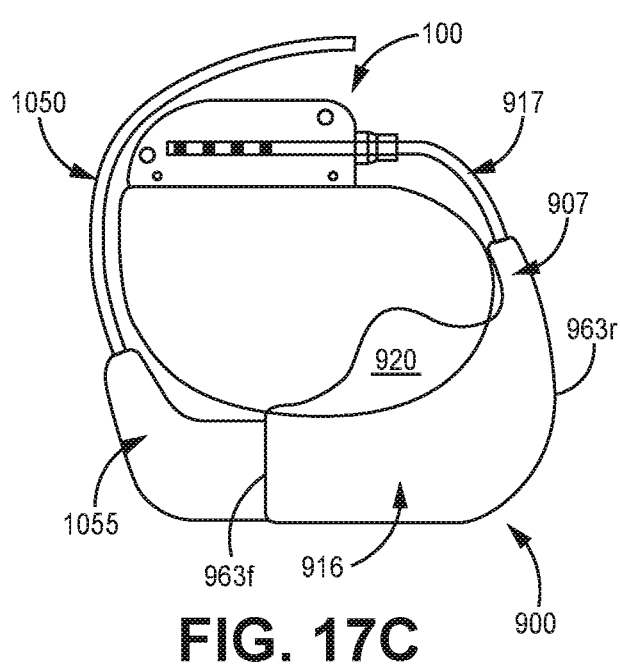
FIG. 17C is a schematic perspective view of an embodiment of the adapter assembly depicted in FIG. 76A, in which the device is held in the casing.
Figure 18:
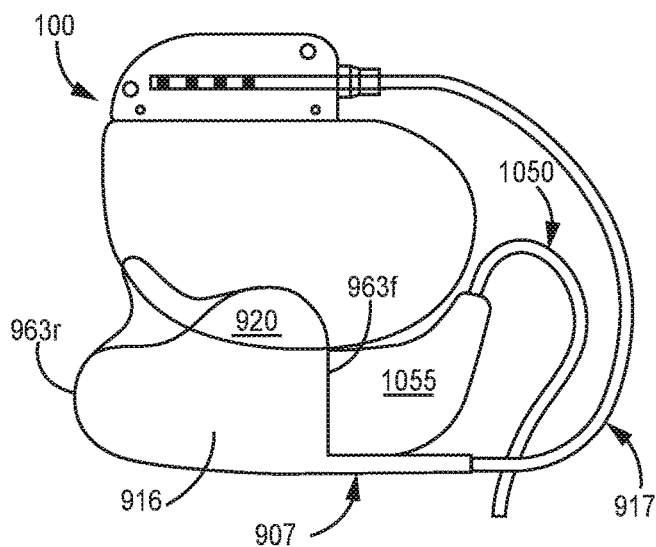
FIG. 18 is a schematic side view of an embodiment of an adapter assembly including an adapter connection module and a casing holding an electrical device.
Figure 19:
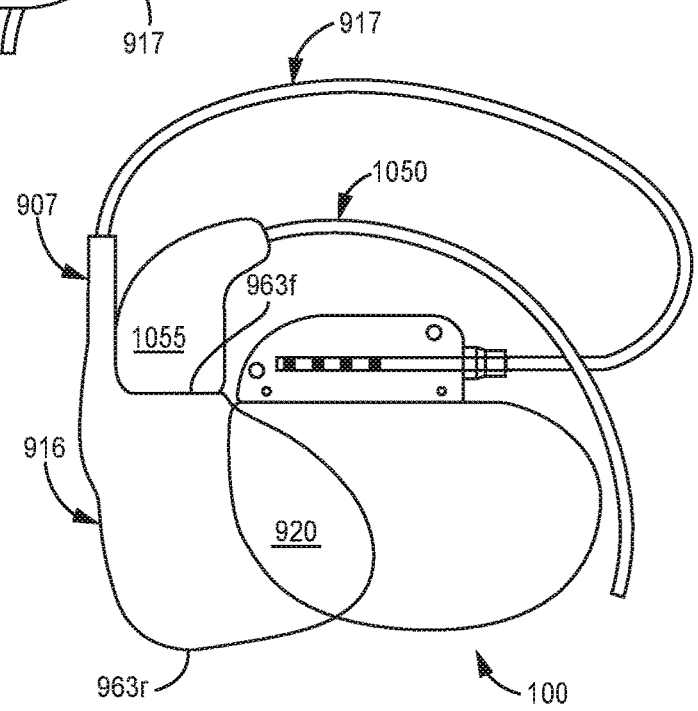
FIG. 19 is a schematic side view of an embodiment of an adapter assembly including an adapter connection module and a casing holding an electrical device.
Figure 20:
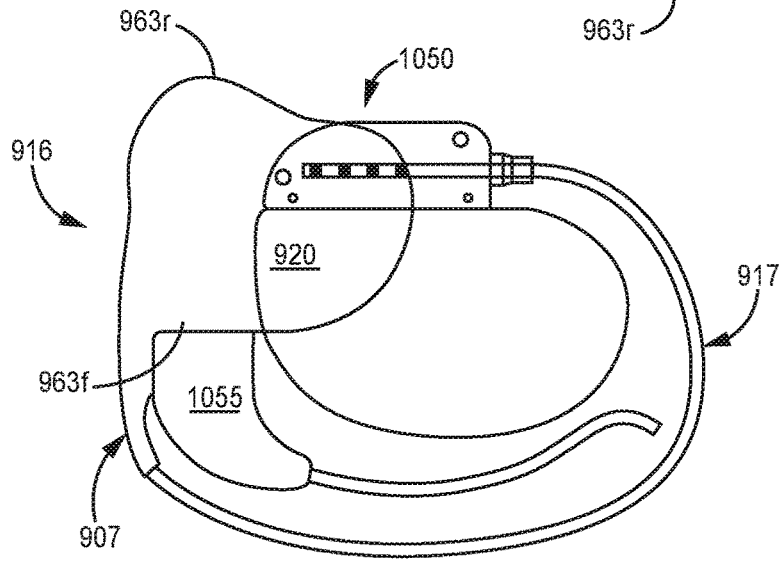
FIG. 20 is a schematic side view of an embodiment of an adapter assembly including an adapter connection module and a casing holding an electrical device.

FIG. 17A-B further illustrates assembly 900 including an elongate collar 907 extending from an intersection of module perimeter edge rear portion 963r and bottom portion 963b, wherein collar 907 provides for attachment of terminal connector 917 to assembly 900, as shown in FIG. 17C. Module 916, collar 907, and clip plates 921, 922 of adapter assembly 900 may be integrally formed from a relatively rigid medical grade plastic, for example, polyurethane or polysulfone, and terminal connector 917 attached thereto by any suitable method known to those skilled in the art. With reference to FIG. 17C, it should be understood that each of the conductors of assembly 900 has a first end coupled to a corresponding internal electrical contact of ports 965 and a second end coupled to a corresponding external contact of terminal connector 917. FIGS. 18-20 show various other configurations for alternate embodiments of assembly 900.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising" and the like. As used herein, "consisting essentially of," as it relates to an article, means that the components of the article are limited to the enumerated components and any other components that do not materially affect the basic and novel characteristic(s) of the article.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

Any direction referred to here, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

In the foregoing detailed description, the invention has been described with reference to specific embodiments. However, it may be appreciated that various modifications and changes can be made without departing from the scope of the invention as set forth in the appended claims. Furthermore various combinations of elements described above in conjunction with the specific embodiments, are within the scope of the present invention, for example, according to the appended claims.

The invention claimed is:

1. An implantable casing for securing an implantable adapter connector module and an implantable medical device together within a subcutaneous pocket of a patient, the casing comprising:

opposing first and second plates spaced apart from one another by a gap configured to receive the adapter connector module and the medical device; and a sidewall joining the first plate to the second plate to define the gap, wherein the gap between the first and second plates has one or more entry openings defined by portions of the first and second plate that are not joined together by the sidewall, and wherein the first plate and the second plate are spring biased toward one another such that, when the device and the adapter connector module are received in the gap, sides of the device and adapter connector module are in confronting engagement with, and secured by, the first and second plates and a connector port opening of the adapter connector module faces generally toward one of the one or more entry openings.

2. The implantable casing of claim 1, where the gap is configured to retain the adapter connector module and the device such that a bottom perimeter edge of the adapter connector module abuts or is spaced apart from a top perimeter edge of the device.

3. The implantable casing of claim 1, wherein the gap includes a device compartment configured to receive the device and includes an adapter compartment configured to receive the adapter connector module.

4. The casing of claim 3, wherein the adapter compartment of the gap extends to perimeter edge top portions of the first and second plates, and the device compartment of the gap extends to perimeter edge bottom portions of the first and second plates, wherein the perimeter edge rear portions of the first and second plates are joined by the sidewall, and wherein the perimeter edge front portions of the first and second plates define one of the one or more entry openings.

5. The casing of claim 4, wherein the perimeter edge bottom portions of the first and second plates define another of the one or more gap entry openings.

6. The casing of claim 4, wherein the perimeter edge top portions of the first and second plates extend toward one another.

7. The casing of claim 1, wherein the first and second plates are elastically deformable.

8. The casing of claim 1, wherein one or both of the first and second plates has an aperture formed therethrough.

9. The casing of claim 1, further comprising a pin member configured to join a free perimeter edge of the first plate to a free perimeter edge of the second plate.

10. The casing of claim 1, wherein at least a portion of the sidewall has a contour matching a contour of a rear perimeter edge of the device.

11. The casing of claim 10, wherein another portion of the sidewall has a contour matching a contour of a rear perimeter edge of the adapter connector module.

12. The casing of claim 8, wherein the casing is configured such that, when the device and the adapter connector module are received in the gap, a side of the device or adapter connector module is exposed through the aperture.

* * * * *